(12) United States Patent
Ylitalo et al.

(10) Patent No.: US 8,696,975 B2
(45) Date of Patent: Apr. 15, 2014

(54) METHODS OF MAKING SHAPED POLYMERIC MATERIALS

(75) Inventors: Caroline M. Ylitalo, Stillwater, MN (US); Robin E. Wright, Inver Grove Heights, MN (US); Matthew T. Scholz, Woodbury, MN (US); Narina Y. Stepanova, Inver Grove Heights, MN (US); Jessica M. Buchholz, Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 547 days.

(21) Appl. No.: 12/747,182

(22) PCT Filed: Dec. 8, 2008

(86) PCT No.: PCT/US2008/085809
§ 371 (c)(1),
(2), (4) Date: Aug. 11, 2010

(87) PCT Pub. No.: WO2009/076267
PCT Pub. Date: Jun. 18, 2009

(65) Prior Publication Data
US 2010/0295219 A1 Nov. 25, 2010

Related U.S. Application Data

(60) Provisional application No. 61/015,255, filed on Dec. 20, 2007, provisional application No. 61/013,300, filed on Dec. 12, 2007, provisional application No. 61/013,085, filed on Dec. 12, 2007.

(51) Int. Cl.
*B29C 35/08* (2006.01)
*C08F 299/02* (2006.01)

(52) U.S. Cl.
USPC .................................. 264/496; 264/343

(58) Field of Classification Search
USPC ..................................... 264/496, 343
See application file for complete search history.

(56) References Cited

U.S. PATENT DOCUMENTS

| 1,529,256 A | 3/1925 | Kelley |
| RE24,906 E | 12/1960 | Ulrich |
| 3,121,021 A | 2/1964 | Copeland |

(Continued)

FOREIGN PATENT DOCUMENTS

| DE | 101 14 498 | 9/2002 |
| EP | 0 201 214 | 11/1986 |

(Continued)

OTHER PUBLICATIONS

Andreopoulos, "Photoscissable hydrogel synthesis via rapid photopolymerization of novel PEG-based polymers in the absence of photoinitiators", *J. Am. Chem. Soc.*, vol. 118, No. 26, pp. 6235-6240 (Jul. 3, 1996).

(Continued)

*Primary Examiner* — Ryan Ochylski
(74) *Attorney, Agent, or Firm* — Stephen L. Crooks

(57) ABSTRACT

The present disclosure describes methods for making shaped polymeric materials. Methods are provided for making shaped polymeric materials from a precursor composition that contains a polar solvent and a polymerizable material that is miscible with the polar solvent. The precursor composition is at least partially polymerized in a mold.

10 Claims, 2 Drawing Sheets

(56) References Cited

U.S. PATENT DOCUMENTS

| | | | |
|---|---|---|---|
| 3,389,827 A | 6/1968 | Abere | |
| 3,645,835 A | 2/1972 | Hodgson | |
| 3,975,350 A | 8/1976 | Hudgin | |
| 4,112,213 A | 9/1978 | Waldman | |
| 4,157,418 A | 6/1979 | Heilmann | |
| 4,231,370 A | 11/1980 | Mroz | |
| 4,351,922 A | 9/1982 | Yoshida | |
| 4,351,992 A | 9/1982 | Crouch | |
| 4,444,961 A * | 4/1984 | Timm | 526/88 |
| 4,499,896 A | 2/1985 | Heinecke | |
| 4,542,176 A | 9/1985 | Graham | |
| 4,597,975 A | 7/1986 | Woodward | |
| 4,598,004 A | 7/1986 | Heinecke | |
| 4,646,730 A | 3/1987 | Schonfeld | |
| 4,726,989 A | 2/1988 | Mrozinski | |
| 4,814,131 A | 3/1989 | Atlas | |
| 4,867,881 A | 9/1989 | Kinzer | |
| 4,873,299 A | 10/1989 | Nowakowsky | |
| 4,929,400 A * | 5/1990 | Rembaum et al. | 264/10 |
| 4,971,732 A * | 11/1990 | Wichterle | 264/1.1 |
| 4,988,568 A | 1/1991 | Hasegawa | |
| 5,059,664 A | 10/1991 | Yada | |
| 5,088,483 A | 2/1992 | Heinecke | |
| 5,120,594 A | 6/1992 | Mrozinski | |
| 5,126,381 A * | 6/1992 | Liscomb | 522/3 |
| 5,160,315 A | 11/1992 | Heinecke | |
| 5,175,030 A | 12/1992 | Lu | |
| 5,260,360 A | 11/1993 | Mrozinski | |
| 5,435,816 A | 7/1995 | Spurgeon | |
| 5,437,932 A | 8/1995 | Ali | |
| 5,447,727 A | 9/1995 | Graham | |
| 5,484,863 A | 1/1996 | Molock | |
| 5,506,279 A | 4/1996 | Babu | |
| 5,506,324 A | 4/1996 | Gartner | |
| 5,514,379 A | 5/1996 | Weissleder | |
| 5,531,855 A | 7/1996 | Heinecke | |
| 5,667,541 A | 9/1997 | Klun | |
| 5,670,557 A | 9/1997 | Dietz | |
| 5,674,521 A | 10/1997 | Gehrke | |
| 5,674,561 A | 10/1997 | Dietz | |
| 5,690,705 A | 11/1997 | Holmes | |
| 5,714,259 A | 2/1998 | Holmes | |
| 5,733,570 A | 3/1998 | Chen | |
| 5,738,642 A | 4/1998 | Heinecke | |
| 5,779,632 A | 7/1998 | Dietz | |
| 5,849,325 A | 12/1998 | Heinecke et al. | |
| 5,954,869 A | 9/1999 | Elfersy | |
| 5,962,544 A | 10/1999 | Waller, Jr. | |
| 6,066,325 A | 5/2000 | Wallace | |
| 6,297,424 B1 | 10/2001 | Olson | |
| 6,372,407 B1 | 4/2002 | Liu | |
| 6,376,590 B2 | 4/2002 | Kolb | |
| 6,386,699 B1 | 5/2002 | Ylitalo | |
| 6,407,195 B2 | 6/2002 | Sherman | |
| 6,467,897 B1 | 10/2002 | Wu | |
| 6,471,975 B1 | 10/2002 | Banovetz | |
| 6,559,351 B1 | 5/2003 | Eakin | |
| 6,566,575 B1 | 5/2003 | Stickels | |
| 6,649,249 B1 | 11/2003 | Engle | |
| 6,669,981 B2 | 12/2003 | Parsons | |
| 6,709,716 B2 | 3/2004 | Uy | |
| 6,772,708 B2 | 8/2004 | Klofta | |
| 6,800,278 B1 | 10/2004 | Perrault | |
| 6,808,738 B2 | 10/2004 | DiTizio | |
| 6,852,255 B2 | 2/2005 | Yang | |
| 6,905,698 B1 | 6/2005 | Aldcroft | |
| 6,960,275 B2 | 11/2005 | Vesley | |
| 6,967,261 B1 | 11/2005 | Soerens | |
| 7,005,143 B2 | 2/2006 | Abuelyaman | |
| 7,074,063 B1 | 7/2006 | Bailey | |
| 7,105,809 B2 | 9/2006 | Wood | |
| 7,223,364 B1 | 5/2007 | Johnston | |
| 2003/0021961 A1 | 1/2003 | Ylitalo | |
| 2003/0054025 A1 | 3/2003 | Cantor | |
| 2003/0235678 A1 | 12/2003 | Graham | |
| 2004/0086479 A1 | 5/2004 | Grinstaff | |
| 2004/0157971 A1 | 8/2004 | Kim | |
| 2004/0180226 A1 | 9/2004 | Chatterjee | |
| 2004/0229018 A1 | 11/2004 | Graham | |
| 2005/0058821 A1 | 3/2005 | Smith | |
| 2005/0124724 A1 | 6/2005 | Burton | |
| 2005/0215752 A1 | 9/2005 | Popp | |
| 2005/0287191 A1 | 12/2005 | Munro | |
| 2006/0034899 A1 | 2/2006 | Ylitalo | |
| 2006/0035039 A1 | 2/2006 | Ylitalo | |
| 2006/0051384 A1 | 3/2006 | Scholz | |
| 2006/0051385 A1 | 3/2006 | Scholz | |
| 2006/0052452 A1 | 3/2006 | Scholz | |
| 2006/0062854 A1 | 3/2006 | Chandra | |
| 2006/0127435 A1 | 6/2006 | Van Voris | |
| 2006/0148950 A1 | 7/2006 | Davidson | |
| 2006/0155057 A1 | 7/2006 | Hermeling | |
| 2006/0212011 A1 | 9/2006 | Popp | |
| 2006/0235141 A1 | 10/2006 | Riegel | |
| 2007/0031505 A1 * | 2/2007 | Roy et al. | 424/490 |
| 2007/0048505 A1 | 3/2007 | Shimada | |
| 2007/0188864 A1 | 8/2007 | Duncan | |
| 2008/0207794 A1 | 8/2008 | Wright | |
| 2008/0300339 A1 | 12/2008 | Wright | |
| 2010/0266794 A1 | 10/2010 | Wright | |

FOREIGN PATENT DOCUMENTS

| | | |
|---|---|---|
| EP | 0 233 667 | 8/1987 |
| EP | 0 317 858 | 11/1988 |
| EP | 0 374 807 | 6/1990 |
| EP | 0 679 333 | 11/1995 |
| EP | 1 371 668 | 12/2003 |
| JP | S52-047883 | 4/1977 |
| JP | 54-074886 | 6/1979 |
| JP | 6-248107 | 9/1994 |
| JP | 7-133355 | 5/1995 |
| JP | 10-018125 | 1/1998 |
| JP | 2002-180361 | 6/2002 |
| JP | 2002-322203 | 8/2002 |
| JP | 2003-034703 | 2/2003 |
| KR | 2001-016592 | 3/2001 |
| KR | 2003-45730 | 6/2003 |
| WO | WO 93/21237 | 10/1993 |
| WO | WO 99/56542 | 11/1999 |
| WO | WO 00/73082 | 12/2000 |
| WO | WO 00/73083 | 12/2000 |
| WO | WO 00/78830 | 12/2000 |
| WO | WO 01/02093 | 1/2001 |
| WO | WO 01/41818 | 6/2001 |
| WO | WO 01/56625 | 8/2001 |
| WO | WO 02/078756 | 10/2002 |
| WO | WO 03/061538 | 7/2003 |
| WO | WO 2004/028255 | 4/2004 |
| WO | WO 2004/105687 | 12/2004 |
| WO | WO 2005/062018 | 7/2005 |
| WO | WO 2006/002641 | 1/2006 |
| WO | WO 2006/027702 | 3/2006 |
| WO | WO 2006/027703 | 3/2006 |
| WO | WO 2006/079631 | 8/2006 |
| WO | WO 2006/011062 | 12/2006 |
| WO | WO 2007/018422 | 2/2007 |
| WO | WO 2007/070310 | 6/2007 |
| WO | WO 2007/146722 | 12/2007 |

OTHER PUBLICATIONS

Andreopoulos, "Light-indusing tailoring of PEG-hydrogel properties", *Biomaterials*, vol. 19, No. 15, pp. 1343-1352, (Aug. 31, 1998).

Barrett, *PMSE Preprints*, "Microcontact Printing of Poly(organophosphazenes): Potential Applications for Selective Cell Adhesion" vol. 91, pp. 633-634 (2004).

Calvert, *224th ACS National Meeting*, Abstract MTLS-008 (Aug. 2002).

DiRamio, "Poly(ethylene glycol) Methacrylate/Dimethacrylate Hydrogels for Controlled Release of Hydrophobic Drugs," *Biotechnol. Prog.*, vol. 21, No. 4, pp. 1281-1288 (2005).

(56) References Cited

OTHER PUBLICATIONS

Drtina, "Highly Cross-Linked Azlactone Functional Supports of Tailorable Polarity," *Macromolecules*, vol. 29, No. 13, pp. 4486-4489 (1996).

Hahn, "Photolithographic patterning of polyethylene glycol hydrogels", *Biomaterials*, vol. 27, No. 12, pp. 2519-2524 (2006).

Karp, *Biomaterials 27* (2006), "A photolithographic method to create cellular micropatterns" (Feb. 15, 2006).

Kizilel, "Photopolymerization of Poly(Ethylene Glycol) Diacrylate on Eosin-Functionalized Surfaces," *Langmuir* vol. 20, No. 20, pp. 8652-8658 Sep. 28, 2004).

Lee, "Multilayer Transfer Printing on Microreservoir-Patterned Substrate Employing Hydrophilic Composite Mold for Selective Immobilization of Biomolecules," *Langmuir*, vol. 22, No. 18, pp. 7689-7694 (Aug. 29, 2006).

Lensen, "Micro- and Nanopatterened Star Poly(ethylene glycol) (PEG) Materials Prepared by UV-based Imprint Lithography," *Langmuir*, vol. 23, No. 14, pp. 7841-7846 (2007).

Lin-Gibson, "Synthesis and characterization of poly(ethylene glycol) dimethacrylate hydrogels", *Macromolecular Symposia*, vol. 227, pp. 243-254 (2005).

Mellott, "Release of protein from highly cross-linked hydrogels of poly(ethylene glycol) diacrylate fabricated by UV polymerization", *Biomaterials*, vol. 22, pp. 929-941 (2001).

Russell, "Poly(ethylene glycol) hydrogel-encapsulated fluorophore-enzyme conjugates for direct detection of organophosphorus neurotoxins", *Analytical Chemistry*, vol. 71, No. 21, pp. 4909-4912 (1999).

Sugimoto, "Applicability of UV Curable Urethane Acrylate Coating at High Drawing Speed", *International Wire & Cable Symposium Proceedings*, pp. 418-425 (1997).

Tuncel, Nonswellable and Swellable Poly(EGDMA) Microspheres; *Journal of Applied Polymer Science*, vol. 62, pp. 789-798 (1996).

Wente, "Superfine Thermoplastic Fibers," *Industrial Engineering Chemistry*, vol. 48, pp. 1342-1346 (1956).

Wente, "Manufacture of Super Fine Organic Fibers," *Naval Research Laboratories*, Report No. 4364, (May 25, 1954).

Zhou, *229$^{th}$ ACS National Meeting*, Abstract BIOT-078 (2005).

\* cited by examiner

METHODS OF MAKING SHAPED POLYMERIC MATERIALS

CROSS REFERENCE TO RELATED APPLICATIONS

This application is a national stage filing under 35 U.S.C. 371 of PCT/US2008/085809, filed Dec. 8, 2008, which claims priority to Provisional Application Nos. 61/013,085, 61/013,300, both filed Dec. 12, 2007 and 61/015,255 filed Dec. 20, 2007, the disclosure of which is incorporated by reference in its/their entirety herein.

FIELD

The present disclosure relates to making shaped polymeric materials.

BACKGROUND

Numerous applications are available for polymeric materials having defined shapes in biological uses, medical uses, and industrial uses. There is a continuing need for polymeric materials having defined shapes with unique physical properties, chemical properties, and versatility. Numerous methods for making polymeric materials having defined shapes are known.

Molds for forming polymeric materials with defined shapes are known. A need for forming polymeric materials having defined shapes on a microscopic level is needed in many applications.

SUMMARY

The present disclosure describes methods for making shaped polymeric materials. More specifically, methods are provided for making shaped polymeric materials from a precursor composition that contains a polar solvent and a polymerizable material that is miscible with the polar solvent. The precursor composition is at least partially polymerized in a mold.

In a first aspect, a method is provided for making a shaped polymeric material. The method includes providing a precursor composition comprising at least 10 weight percent of a polar solvent based on the total weight of the precursor composition and no greater than 90 weight percent of a polymerizable material based on the total weight of the precursor composition. The polar solvent comprises water. The polymerizable material forms a single phase with the polar solvent and is capable of free-radical polymerization. The polymerizable material has an average number of ethylenically unsaturated groups per monomer molecule equal to at least 1.2. The polymerizable material comprises a poly(alkylene oxide(meth)acrylate) having at least 2 (meth)acryloyl groups and at least 5 alkylene oxide units. The method further includes providing a mold having at least two separate wells. The precursor composition is added to the mold and positioned in at least a portion of the at least two separate wells. Within the wells, the precursor composition is exposed to radiation to at least partially polymerize the polymerizable material, and to form a first swollen shaped polymeric material.

In a second aspect, a method is provided for making a shaped polymeric material. The method includes providing a precursor composition comprising at least 10 weight percent of a polar solvent based on the total weight of the precursor composition and no greater than 90 weight percent of a polymerizable material based on the total weight of the precursor composition. The polymerizable material forms a single phase with the polar solvent and is capable of free-radical polymerization. The polymerizable material has an average number of ethylenically unsaturated groups per monomer molecule equal to at least 1.2. The polymerizable material comprises a poly(alkylene oxide(meth)acrylate) having at least 2 (meth)acryloyl groups and at least 5 alkylene oxide units. The average molecular weight of the poly(alkylene oxide(meth)acrylate) is less than 2,000 g/mole. The method further includes providing a mold having at least two separate wells. The precursor composition is added to the mold, and positioned in at least a portion of the at least two separate wells. Within the wells, the precursor composition is exposed to radiation to at least partially polymerize the polymerizable material, and to form a first swollen shaped polymeric material.

DETAILED DESCRIPTION

Figure 1:
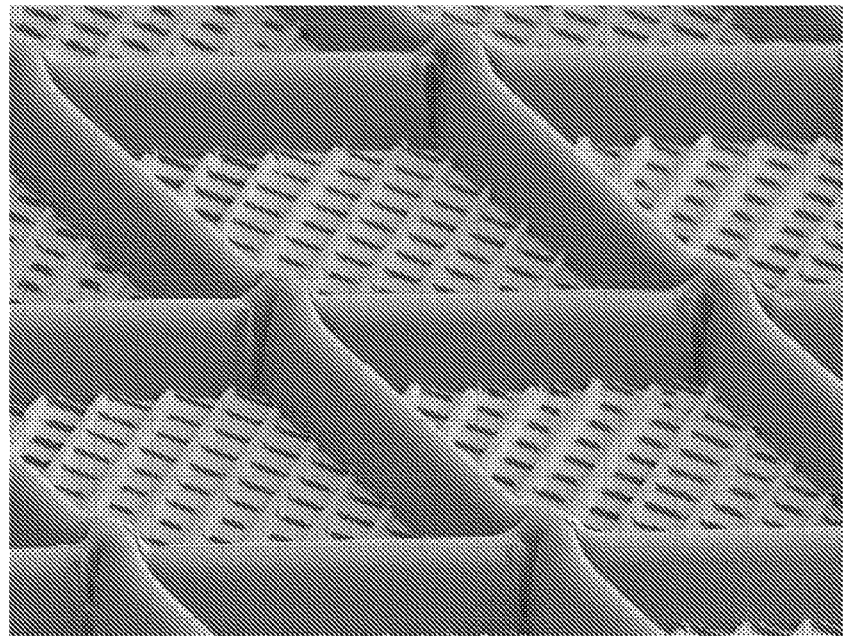
FIG. 1 is an optical micrograph of a mold having at least two wells of Example 1.

Although the present disclosure is herein described in terms of specific embodiments, it will be readily apparent to those skilled in the art that various modifications, rearrangements, and substitutions can be made without departing from the spirit of the invention. The scope of the present invention is thus only limited by the claims appended hereto.

The recitation of numerical ranges by endpoints includes all numbers subsumed within that range (e.g., 1 to 5 includes 1, 1.5, 2, 2.75, 3, 3.8, 4, and 5).

As included in this specification and the appended claims, the singular forms "a", "an", and "the" include plural referents unless the content clearly dictates otherwise. Thus, for example, reference to a composition containing "a compound" includes a mixture of two or more compounds. As used in this specification and appended claims, the term "or" is generally employed in its sense including "and/or" unless the content clearly dictates otherwise.

Unless otherwise indicated, all numbers expressing quantities or ingredients, measurement of properties and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present disclosure. At the very least, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains errors necessarily resulting from the standard deviations found in their respective testing measurements.

The precursor composition useful for making shaped polymeric materials comprises a polar solvent and a polymerizable material that is miscible in the polar solvent. The polymerizable material has ethylenically unsaturated groups which can be at least partially polymerized when exposed to radiation. The precursor composition is added to a mold having at least two separate wells, and then exposed to radiation to at least partially polymerize the polymerizable material to form a swollen shaped polymeric material. The swollen shaped polymeric material has a shape and dimensions similar to the wells of the mold.

Hydrogels are commonly referred to as a network of hydrophilic polymer chains that are water insoluble, sometimes found as a colloidal gel in which water is the dispersion medium. Hydrogels are superabsorbent natural or synthetic polymers and can be swollen or are capable of being swollen with a polar solvent (e.g., water). Some hydrogels can be swollen with polar solvents other than water. Shaped polymeric materials of this disclosure are referred to as hydrogels. Shaped polymeric materials can be swollen with water or with a polar solvent other than water to form swollen shaped polymeric materials. Swollen shaped polymeric materials can be dried to remove at least some of the polar solvent to form dried shaped polymeric materials. The swollen shaped polymeric materials and the dried shaped polymeric materials generally contain crosslinked polymer chains.

Precursor compositions can be added to molds for making shaped polymeric materials. The precursor composition can be at least partially polymerized by applied radiation. The at least partially polymerized compositions can form swollen shaped polymeric materials (e.g., crosslinked hydrogels). In some examples, the precursor composition may be completely polymerized to form swollen shaped polymeric materials.

The precursor composition for making shaped polymeric materials comprises a polar solvent and a polymerizable material. The precursor composition comprises at least 10 weight percent of a polar solvent based on the total weight of the precursor composition, and no greater that 90 weight percent polymerizable material based on the total weight of the precursor composition. The polymerizable material is capable of free-radical polymerization when exposed to radiation. The polymerizable material has an average number of ethylenically unsaturated groups per monomer molecule equal to at least 1.2, and the polymerizable material forms a single phase with the polar solvent. The polymerizable material comprises a poly(alkylene oxide(meth)acrylate) having at least 2 (meth)acryloyl groups and at least 5 alkylene oxide units. In some embodiments, the polar solvent comprises water. In other embodiments, the polar solvent may not comprise water.

In one aspect, the precursor composition contains a polar solvent comprising water and a polymerizable material.

In a second aspect, the precursor composition comprises a polar solvent and a polymerizable material containing a poly(alkylene oxide(meth)acrylate) having at least 2 (meth)acryloyl groups, at least 5 alkylene oxide units, and an average molecular weight less than 2,000 g/mole. The polar solvent does not necessarily comprise water.

The polar solvent of the precursor composition may contain water, a water-miscible organic solvent, or a mixture thereof. The polar solvent is generally not reactive in the precursor composition, such that the polar solvent typically swells the resulting shaped polymeric material. In some instances, the polar solvent may be involved in chain transfer reactions. The polymerizable material is at least partially polymerized in the presence of the polar solvent resulting in a shaped polymeric material swollen with the polar solvent. Swollen shaped polymeric materials generally contain at least some of the polar solvent of the precursor composition.

The polar solvent can be tap water, well water, deionized water, spring water, distilled water, sterile water, sea water, inorganic aqueous buffer solutions, organic aqueous buffer solutions or any other suitable type of water. A water miscible organic solvent refers to an organic solvent that is typically capable of hydrogen bonding and forms a single phase solution when mixed with water at 23° C. Water miscible solvents often contain hydroxyl or oxy groups. Water miscible solvents are often alcohols, polyols having a weight average molecular weight no greater than about 300 g/mole, ethers, or polyethers having a weight average molecular weight no greater than 300 g/mole. Some examples of water miscible solvents include, but are not limited to, methanol, ethanol, isopropanol, n-propanol, ethylene glycol, triethylene glycol, glycerol, polyethylene glycol, propylene glycol, dipropylene glycol, polypropylene glycol, random and block copolymers of ethylene oxide and propylene oxide, dimethyoxytetraglycol, butoxytriglycol, trimethylene glycol trimethyl ether, ethylene glycol dimethyl ether, ethylene glycol monobutyl ether, ethylene glycol monoethyl ether, ethylene carbonate, dimethylformamide, N-methylpyrrolidinone, urea, and mixtures thereof. The polar solvent can be a liquid, or a melted solid at or above 23° C.

The polar solvent present in the precursor composition is at least 10 weight percent based on the total weight of the precursor composition. In some precursor compositions, the polar solvent present in the precursor composition can be at least 15 weight percent, at least 20 weight percent, at least 25 weight percent, at least 40 weight percent, or at least 50 weight percent based on the total weight of the precursor composition. The polar solvent present in the precursor composition can be in an amount up to 90 weight percent, up to 85 weight percent, up to 80 weight percent, up to 65 weight percent, or up to 60 weight percent based on the total weight of the precursor composition. The polar solvent present in the precursor composition can be in a range of 10 to 90 weight percent, 10 to 85 weight percent, 15 to 80 weight percent, or in a range of 20 to 65 percent based on the total weight of the precursor composition.

In addition to the polar solvent, the precursor composition includes a polymerizable material that is miscible with the polar solvent. Polymerizable material generally refers to a monomer or to a mixture of monomers. The terms "monomer" and "monomer molecule" are used interchangeably to refer to a compound that contains at least one polymerizable group capable of free-radical polymerization. The polymerizable group is usually an ethylenically unsaturated group.

The polymerizable material includes a monomer of a single chemical structure, or it may include a plurality of different monomers (i.e., there is a mixture of monomers having different chemical structures). Whether the polymerizable material includes one monomer or a mixture of monomers, the polymerizable material has an average number of polymerizable groups (e.g., ethylenically unsaturated groups) per monomer molecule equal to at least 1.2. The polymerizable material can include, for example, a single type of monomer that has two or more polymerizable groups. Alternatively, the polymerizable material can include a plurality of different types of monomers such that the average number of polymerizable groups per monomer molecule is equal to at least 1.2. In some embodiments, the average number of polymerizable groups per monomer molecule is equal to at least 1.3, at least 1.4, at least 1.5, at least 1.6, at least 1.7, at least 1.8, at least 1.9, at least 2.0, at least 2.1, at least 2.2, at least 2.3, at least 2.4, at least 2.5, at least 2.6, at least 2.7, at least 2.8, at least 2.9, or at least 3.0.

The average number of polymerizable groups per molecule is determined by calculating the relative molar concentration of each monomer molecule and its functionality (number of polymerizable groups). For example, a polymerizable material that contains X mole percent of a first monomer having n polymerizable groups and (100−X) mole percent of a second monomer having m polymerizable groups has an average number of polymerizable groups per monomer molecule equal to [n(X)+m(100−X)]/100. In another example, a polymerizable material that contains X mole percent of a first monomer having n polymerizable groups, Y mole percent of a second monomer having m polymerizable groups, and (100−X−Y) mole percent of a third monomer having q polymerizable groups has an average number of polymerizable groups per molecule equal to [n(X)+m(Y)+q(100−X−Y)]/100.

The polymerizable material of the precursor composition comprises monomers with ethylenically unsaturated groups capable of free radical polymerization. The polymerizable material forms a single phase with the polar solvent and does not phase separate from the polar solvent at 23° C. The polymerizable material is considered miscible with the polar solvent, such that polymerizable material is predominantly soluble or compatible in the polar solvent. On occasion, there can be a small amount of undissolved polymerizable material in the polar solvent. For example, the polymerizable material may have an impurity that does not dissolve in the polar solvent. Generally, at least 95 weight percent, at least 97 weight percent, at least 98 weight percent, at least 99 weight percent, at least 99.5 weight percent, at least 99.8 weight percent, or at least 99.9 weight percent of the polymerizable material is soluble in the polar solvent. A cured film of the precursor composition is essentially transparent as determined by visible spectroscopy on a cured film having a thickness of 250 micrometers. The cured film from the precursor composition has a light transmission of at least 85 percent or greater at a wavelength of 500 nm The polymerizable material includes at least one monomer having two or more polymerizable groups. Likewise, a first monomer having three or more polymerizable groups can be mixed with a second monomer having one polymerizable group, a second monomer having two polymerizable groups, or a mixture thereof provided that the mixture contains an average number of polymerizable groups per monomer molecule equal to at least 1.2. Often, a monomer nominally having three or more polymerizable groups contains monomeric impurities having two polymerizable groups, one polymerizable group, or a mixture thereof.

The polymerizable material often includes one or more (meth)acrylates. As used herein, the term "(meth)acrylate" refers to a methacrylate, acrylate, or mixture thereof. The (meth)acrylate contains a (meth)acryloyl group. The term "(meth)acryloyl" refers to a monovalent group of formula $H_2C=CR^b-(CO)-$ where Rb is hydrogen or methyl, and (CO) denotes that the carbon is attached to the oxygen with a double bond. The (meth)acryloyl group is the polymerizable group (i.e., the ethylenically unsaturated group) of the (meth)acrylate that is capable of free-radical polymerization. All of the polymerizable materials can be (meth)acrylates or the polymerizable materials can include one or more (meth)acrylates in combination with other monomers that have ethylenically unsaturated groups.

The polymerizable material of the precursor composition includes a poly(alkylene oxide(meth)acrylate). The terms poly(alkylene oxide(meth)acrylate), poly(alkylene glycol (meth)acrylate), alkoxylated(meth)acrylate, and alkoxylated poly(meth)acrylate can be used interchangeably to refer to a (meth)acrylate having at least one group that contains two or more alkylene oxide residue units (also referred to as alkylene oxide units). There are often at least 5 alkylene oxide residue units. The alkylene oxide unit is a divalent group of formula —OR— where R is an alkylene having up to 10 carbon atoms, up to 8 carbon atoms, up to 6 carbon atoms, or up to 4 carbon atoms. The alkylene oxide units are often selected from ethylene oxide units, propylene oxide units, butylene oxide units, or mixtures thereof.

In some embodiments, the polymerizable material includes a poly(alkylene oxide(meth)acrylate) having at least 2 (meth)acryloyl groups per monomer molecule. The poly (alkylene oxide(meth)acrylate) can be used alone or in combination with other monomers to provide an average of at least 1.2 ethylenically unsaturated groups per monomer molecule. The alkoxylated portion (i.e., the poly(alkylene oxide) portion) often has at least 5 alkylene oxide units selected from ethylene oxide units, propylene oxide units, butylene oxide units, or a combination thereof. That is, each mole of the poly(alkylene oxide(meth)acrylate) contains at least 5 moles of alkylene oxide units. The plurality of alkylene oxide units facilitates the solubility of the poly(alkylene oxide(meth) acrylate) in the polar solvent. Some exemplary poly(alkylene oxide(meth)acrylates) contain at least 6 alkylene oxide units, at least 8 alkylene oxide units, at least 10 alkylene oxide units, at least 12 alkylene oxide units, at least 15 alkylene oxide units, at least 20 alkylene oxide units, or at least 30 alkylene oxide units. The poly(alkylene oxide(meth)acrylate) can contain poly(alkylene oxide) chains that are homopolymer chains, block copolymer chains, random copolymer chains, or mixtures thereof. In some embodiments, the poly(alkylene oxide) chains are poly(ethylene oxide) chains.

Any molecular weight of the poly(alkylene oxide(meth) acrylate) having at least 2 (meth)acryloyl groups can be used as long as shaped polymeric materials can be formed from the precursor composition. The weight average molecular weight of the poly(alkylene oxide(meth)acrylate) is often less than 2,000 g/mole, less than 1,800 g/mole, less than 1,600 g/mole, less than 1,400 g/mole, less than 1,200 g/mole, or less than 1,000 g/mole.

The preparation of some exemplary poly(alkylene oxide (meth)acrylates) having multiple (meth)acryloyl groups are described in U.S. Pat. No. 7,005,143 (Abuelyaman et al.), and U.S. Patent Application Publication Nos. 2005/0215752 A1 (Popp et al.), 2006/0212011 A1 (Popp et al.), and 2006/0235141 A1 (Riegel et al.). Suitable poly(alkylene oxide (meth)acrylates) having an average (meth)acryloyl functionality per monomer molecule equal to at least 2 and having at least 5 alkylene oxide units are commercially available, for example, from Sartomer (Exton, Pa.) under the trade designations "SR9035" (ethoxylated (15) trimethylolpropane triacrylate), "SR499" (ethoxylated (6) trimethylolpropane triacrylate), "SR502" (ethoxylated (9) trimethylolpropane triacrylate), "SR415" (ethoxylated (20) trimethylolpropane triacrylate), "CD501" (propoxylated (6) trimethylolpropane triacrylate) and "CD9038" (ethoxylated (30) bis-phenol A diacrylate). The number in parentheses refers to the average number of alkylene oxide units per monomer molecule. Other suitable poly(alkylene oxide(meth)acrylates) include polyalkoxylated trimethylolpropane triacrylates such as those commercially available from BASF (Ludwigshafen, Germany) under the trade designation "LAROMER" with at least 30 alkylene oxide units.

In some embodiments, precursor compositions contain a poly(alkylene oxide(meth)acrylate) having at least 2 (meth)

acryloyl groups per monomer molecule, having at least 5 ethylene oxide units, and a weight average molecular weight less than 2,000 g/mole. The polymerizable material can be the only polymerizable material in the precursor composition or can be combined with other monomers that form a single phase with the polar solvent. Whether the poly(alkylene oxide (meth)acrylate) is the only monomer in the precursor composition or is combined with other monomers, the polymerizable material has an average functionality per monomer molecule equal to at least 1.2.

More specific precursor compositions contain a poly(ethylene oxide) (meth)acrylate having at least 2 (meth)acryloyl groups per monomer molecule, having at least 5 alkylene oxide units, and having a weight average molecular weight less than 2000 g/mole. An even more specific exemplary precursor composition can include an ethoxylated trimethylolpropane triacrylate having a weight average molecular weight less than 2000 g/mole. Often the ethoxylated trimethylolpropane triacrylate contains impurities having one (meth)acryloyl group, two (meth)acryloyl groups, or mixtures thereof. For example, commercially available "SR415" (ethoxylated (20) trimethylolpropane triacrylate), often has an average functionality per monomer molecule less than 3 (when analyzed, the average functionality per monomer molecule was about 2.5). Although impurities may be present, the average functionality per monomer molecule in the precursor composition is equal to at least 1.2.

As long as the average number of ethylenically unsaturated groups (e.g., (meth)acryloyl groups) per monomer molecule is equal to at least 1.2, the polymerizable material can include a single (meth)acrylate (i.e., poly(alkylene oxide(meth)acrylate) or a mixture of (meth)acrylates. To provide an average number of (meth)acryloyl groups per monomer molecule equal to at least 1.2, at least some of the (meth)acrylate present in the polymerizable material has two or more (meth) acryloyl groups per monomer molecule. For example, the polymerizable material can contain a (meth)acrylate having two (meth)acryloyl groups per monomer molecule or can contain a mixture of a (meth)acrylate having two (meth) acryloyl groups per monomer molecule in combination with one or more (meth)acrylates having one (meth)acryloyl group per monomer molecule. In another example, the polymerizable material can contain a (meth)acrylate having two or more (meth)acryloyl groups per monomer molecule and a (meth)acrylate having three (meth)acryloyl groups per monomer molecule, or the polymerizable material can contain a mixture of a (meth)acrylate having two or more (meth)acryloyl groups per monomer molecule, a (meth)acrylate having three (meth)acryloyl groups per monomer molecule in combination with one or more (meth)acrylates having one (meth) acryloyl group per monomer molecule, two (meth)acryloyl groups per monomer molecule, or a mixture thereof.

Specific examples of suitable polymerizable materials with one ethylenically unsaturated group per monomer molecule include, but are not limited to, 2-hydroxyethyl(meth)acrylate, 2-hydroxypropyl(meth)acrylate, 3-hydroxypropyl(meth) acrylate, 4-hydroxybutyl(meth)acrylate, (meth)acrylonitrile, (meth)acrylamide, caprolactone(meth)acrylate, poly(alkylene oxide(meth)acrylate) (e.g., poly(ethylene oxide(meth) acrylate), poly(propylene oxide(meth)acrylate), and poly (ethylene oxide-co-propylene oxide(meth)acrylate)), alkoxy poly(alkylene oxide(meth)acrylate), (meth)acrylic acid, β-carboxyethyl(meth)acrylate, tetrahydrofurfuryl(meth) acrylate, N-vinyl pyrrolidone, N-vinylcaprolactam, N-alkyl (meth)acrylamide (e.g., N-methyl(meth)acrylamide), and N,N-dialkyl(meth)acrylamide (e.g., N,N-dimethyl(meth) acrylamide).

Suitable polymerizable materials with two ethylenically unsaturated groups per monomer molecule include, for example, alkoxylated di(meth)acrylates. Examples of alkoxylated di(meth)acrylates include, but are not limited to, poly(alkylene oxide di(meth)acrylates) such as poly(ethylene oxide di(meth)acrylates) and poly(propylene oxide di(meth) acrylates); alkoxylated diol di(meth)acrylates such as ethoxylated butanediol di(meth)acrylates, propoxylated butanediol di(meth)acrylates, and ethoxylated hexanediol di(meth)acrylates; alkoxylated trimethylolpropane di(meth)acrylates such as ethoxylated trimethylolpropane di(meth)acrylate and propoxylated trimethylolpropane di(meth)acrylate; and alkoxylated pentaerythritol di(meth)acrylates such as ethoxylated pentaerythritol di(meth)acrylate and propoxylated pentaerythritol di(meth)acrylate.

Examples of suitable polymerizable materials with three ethylenically unsaturated groups per monomer molecule include, for example, alkoxylated tri(meth)acrylates. Examples of alkoxylated tri(meth)acrylates include, but are not limited to, alkoxylated trimethylolpropane tri(meth)acrylates such as ethoxylated trimethylolpropane tri(meth)acrylates, propoxylated trimethylolpropane tri(meth)acrylates, and ethylene oxide/propylene oxide copolymer trimethylolpropane tri(meth)acrylates; and alkoxylated pentaerythritol tri(meth)acrylates such as ethoxylated pentaerythritol tri (meth)acrylates.

Suitable polymerizable materials with at least four ethylenically unsaturated groups per monomer include, for example, alkoxylated tetra(meth)acrylates and alkoxylated penta(meth)acrylates. Examples of alkoxylated tetra(meth) acrylates include alkoxylated pentaerythritol tetra(meth) acrylates such as ethoxylated pentaerythritol tetra(meth) acrylates.

In addition to the precursor composition containing a poly (alkylene oxide(meth)acrylate) having at least 2 (meth)acryloyl groups per monomer molecule, the precursor composition can include other monomers that are added to impart certain characteristics to the shaped polymeric material. In some instances, the precursor composition can contain an anionic monomer. As used herein, the term "anionic monomer" refers to a monomer that contains an ethylenically unsaturated group in addition to an acidic group selected from a carboxylic acid (i.e., carboxy) group (—COOH) or a salt thereof, a sulfonic acid group (—SO$_3$H) or a salt thereof, a sulfate group (—SO$_4$H) or a salt thereof, a phosphonic acid group (—PO$_3$H$_2$) or a salt thereof, a phosphate group (—OPO$_3$H) or a salt thereof, or a mixture thereof. Depending on the pH of the precursor composition, the anionic monomer can be in a neutral state (acidic form) or in the form of a salt (anionic form). The counterions of the anionic form are often selected from alkali metals, alkaline earth metals, ammonium ion, or an ammonium ion substituted with various alkyl groups such as a tetraalkylammonium ion.

Suitable anionic monomers having carboxy groups include, but are not limited to, acrylic acid, methacrylic acid, and various carboxyalkyl(meth)acrylates such as 2-carboxyethylacrylate, 2-carboxyethylmethacrylate, 3-carboxypropylacrylate, and 3-carboxypropylmethacrylate. Other suitable anionic monomers with carboxy groups include (meth)acryloylamino acids such as those described in U.S. Pat. No. 4,157,418 (Heilmann et al.). Exemplary (meth)acryloylamino acids include, but are not limited to, N-acryloylglycine, N-acryloylaspartic acid, N-acryloyl-β-alanine, and 2-acrylamidoglycolic acid. Suitable anionic monomers having sulfonic acid groups include, but are not limited to, various (meth)acrylamidosulfonic acids such as N-acrylamidomethanesulfonic acid, 2-acrylamidoethanesulfonic acid, 2-acrylamido-2-methylpropanesulfonic acid, and 2-methacrylamido-2-methylpropanesulfonic acid. Suitable anionic monomers having phosphonic acid groups include, but are not limited to, (meth)acrylamidoalkylphosphonic acids such as 2-acrylamidoethylphosphonic acid and 3-methacrylamidopropylphosphonic acid. Some suitable anionic monomers having phosphate groups include phosphates of alkylene glycol(meth)acrylates such as phosphates of ethylene glycol (meth)acrylate and phosphates of propylene glycol(meth) acrylate. Salts of any of these acidic monomers can also be used.

The anionic monomer, if present in a precursor composition, can affect the degree, the rate or combinations thereof, of the swelling of the shaped polymeric material, or. That is, the degree of swelling can often be altered by varying the amount of the anionic monomer as well as the amount of other hydrophilic monomer(s) in the precursor composition. The degree of swelling is usually proportional to the total amount of polar solvent that can be sorbed by the shaped polymeric material. The amount of the anionic monomer is controlled so that the average number of ethylenically unsaturated groups per monomer molecule of polymerizable material is at least 1.2. The anionic monomer may be present in an amount ranging from 0 to less than 50 weight percent based on the total weight of the polymerizable material. The polymerizable material may contain at least 1 weight percent, at least 2 weight percent, at least 3 weight percent, or at least 5 weight percent anionic monomer. The polymerizable material may contain up 50 weight percent, up to 25 weight percent, up to 15 weight percent, or up to 10 weight percent anionic monomer. The polymerizable material may contain 0 to 50 weight percent, 0 to 25 weight percent, 0 to 15 weight percent, or 0 to 10 weight percent anionic monomer. Some polymerizable materials do not contain an anionic monomer. Low levels or the complete absence of anionic monomer(s) may be found in precursor compositions containing certain biologically active agents. For example, certain cationic antimicrobial agents may be too tightly bound within the shaped polymeric material to elute or diffuse from a shaped polymeric material as desired.

In some embodiments, the precursor composition may include a cationic monomer. As used herein, the term "cationic monomer" refers to a monomer having an ethylenically unsaturated group as well as an amino group, a salt of an amino group, or a mixture thereof. For example, the cationic monomer can be an amino(meth)acrylate or an amino(meth) acrylamide. The amino group can be a primary amino group or a salt thereof, a secondary amino group or a salt thereof, a tertiary amino group or a salt thereof, or a quaternary salt. The cationic monomers often include a tertiary amino group or a salt thereof or a quaternary amino salt. Depending on the pH of the precursor composition, some cationic monomer can be in a neutral state (basic form) or in the form of a salt (cationic form). The counterions of the cationic form are often selected from halides (e.g., bromides or chlorides), sulfates, alkylsulfates (e.g., methosulfate or ethosulfate), as well as various carboxylate anions (e.g., acetate).

Examples of some amino(meth)acrylates include N,N-dialkylaminoalkyl(meth)acrylates and N-alkylaminoalkyl (meth)acrylates such as, for example, N,N-dimethylaminoethylmethacrylate, N,N-dimethylaminoethylacrylate, N,N-diethylaminoethylmethacylate, N,N-diethylaminoethylacrylate, N,N-dimethylaminopropylmethacrylate, N,N-dimethylaminopropylacrylate, N-tert-butylaminopropylmethacrylate, and N-tert-butylaminopropylacrylate.

Exemplary amino(meth)acrylamides include, for example, N-(3-aminopropyl)methacrylamide, N-(3-aminopropyl) acrylamide, N-[3-(dimethylamino)propyl]methacrylamide, N-(3-imidazolylpropyl)methacrylamide, N-(3-imidazolylpropyl)acrylamide, N-(2-imidazolylethyl)methacrylamide, N-(1,1-dimethyl-3-imidazolylpropyl)methacrylamide, N-(1, 1-dimethyl-3-imidazolylpropyl)acrylamide, N-(3-benzoimidazolylpropyl)acrylamide, and N-(3-benzoimidazolylpropyl)methacrylamide.

Exemplary monomeric quaternary salts include, but are not limited to, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Other exemplary monomeric quaternary amino salts include a dimethylalkylammonium group with the alkyl group having 2 to 22 carbon atoms or 2 to 20 carbon atoms. That is, the monomer includes a group of formula —N(CH$_3$)$_2$ (C$_n$H$_{2n+1}$)$^+$ where n is an integer having a value of 2 to 22. Exemplary monomers include, but are not limited to monomers of the following formula

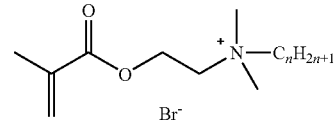

such that n is an integer in the range of 2 to 22. The synthesis of these monomers is described in U.S. Pat. No. 5,437,932 (Ali et al.).

Some cationic monomers, such as those having a quaternary amino group, can impart antimicrobial properties to the shaped polymeric material. The cationic monomer is often present in an amount ranging from 0 to 50 weight percent based on the total weight of the polymerizable material. The polymerizable material may contain at least 0 weight percent, at least 1 weight percent, at least 2 weight percent, or at least 5 weight percent cationic monomer. The polymerizable material may contain up to 50 weight percent, up to 30 weight percent, up to 20 weight percent, up to 15 weight percent, or up to 10 weight percent cationic monomer. The polymerizable material may contain 0 to 50 weight percent, 1 to 30 weight percent, 2 to 20 weight percent, or 5 to 10 weight percent cationic monomer. Some polymerizable materials do not contain a cationic monomer.

Some exemplary polymerizable materials contain only nonionic monomers. That is, the polymerizable material is substantially free of both anionic monomers and cationic monomers. As used herein with reference to the anionic or cationic monomers, "substantially free" means that the polymerizable material contains less than 1 weight percent, less than 0.5 weight percent, less than 0.2 weight percent, or less than 0.1 weight percent anionic monomer or cationic monomer based on the total weight of the polymerizable material.

The precursor composition generally contains no greater than 90 weight percent polymerizable material based on the total weight of the precursor composition. For example, the precursor composition contains at least 10 weight percent, at least 20 weight percent, at least 25 weight percent, at least 30 weight percent, at least 40 weight percent, or at least 50 weight percent polymerizable material. The precursor composition contains no greater than 90 weight percent, no greater than 80 weight percent, no greater than 75 weight percent, no greater than 70 weight percent, or no greater than 60 weight percent polymerizable material. In some precursor compositions, the amount of polymerizable material is in the range of 10 to no greater than 90 weight percent, 20 to no greater than 90 weight percent, 30 to no greater than 90 weight percent, or 50 to no greater than 80 weight percent based on the total weight of the precursor composition.

In addition to the polar solvent and the polymerizable material, the precursor composition may include one or more optional additives such as processing agents, active agents, or mixtures thereof. Any of these optional additives can be dissolved or dispersed in the precursor composition.

The term "processing agent" refers to a compound or mixture of compounds that is added primarily to alter the physical or chemical characteristics of either the precursor composition or the shaped polymeric material. That is, the processing agent is added for the purpose of altering the precursor composition or facilitating the formation of the shaped polymeric material. If added, the processing agent is typically added to the precursor composition. These processing agents are typically not considered to be active agents.

Suitable processing agents include, but are not limited to, rheology modifiers such as polymeric thickeners (such as gum, cellulose, pectin, and the like) or inorganic thickeners (such as clays, silica gels, and the like), surfactants that modify the surface tension, emulsifiers that stabilize the precursor composition, solubilizers that enhance the solubility of the polymerizable material in the polar solvent, initiators to facilitate polymerization of the polymerizable material, chain transfer or retarding agents, binders, dispersants, fixatives, foaming agents, flow aids, foam stabilizers, foam boosters, gellants, glossers, propellants, waxes, compounds to depress the freezing point and/or increase the boiling point of the precursor composition, and plasticizers.

An optional processing agent can be present in an amount no greater than 20 weight percent, no greater than 15 weight percent, no greater than 10 weight percent, no greater than 8 weight percent, no greater than 6 weight percent, no greater than 4 weight percent, no greater than 2 weight percent, no greater than 1 weight percent, or no greater than 0.5 weight percent based on the total weight of the precursor composition.

An initiator is a processing agent found in most precursor compositions for the free-radical polymerization reaction. The initiator can be a photoinitiator, a thermal initiator, or a redox couple. The initiator can be either soluble in the precursor composition or dispersed in the precursor composition.

An example of a suitable soluble photoinitiator is 2-hydroxy-1-[4-(2-hydroxyethoxy)phenyl]-2-methyl-1-propanone, which is commercially available under the trade designation IRGACURE 2959 from Ciba Specialty Chemicals (Tarrytown, N.Y.). An example of a suitable dispersed photoinitiator is alpha, alpha-dimethoxy-alpha-phenylacetophenone, which is commercially available under the trade designation IRGACURE 651 from Ciba Specialty Chemicals. Other suitable photoinitiators are the acrylamidoacetyl photoinitiators, described in U.S. Pat. No. 5,506,279 (Babu et al.) that contain a polymerizable group as well as a group that can function as an initiator.

Suitable thermal initiators include, for example, azo compounds, peroxides or hydroperoxides, persulfates, or the like. Exemplary azo compounds include 2,2'-azobis[2-(2-imidazolin-2-yl)propane]dihydrochloride, 2,2'-azobis(2-amidinopropane)dihydrochloride, and 4,4'-azobis-(4-cyanopentanoic acid). Examples of commercially available thermal azo compound initiators include materials available from DuPont Specialty Chemical (Wilmington, Del.) under the "VAZO" trade designation such as "VAZO 44", "VAZO 56", and "VAZO 68". Suitable peroxides and hydroperoxides include acetyl peroxide, t-butyl hydroperoxide, cumene hydroperoxide, and peroxyacetic acid. Suitable persulfates include, for example, sodium persulfate and ammonium persulfate.

In other examples, the free radical initiator is a redox couple such as ammonium or sodium persulfate and N,N,N', N'-tetramethyl-1,2-diaminoethane; ammonium or sodium persulfate and ferrous ammonium sulfate; hydrogen peroxide and ferrous ammonium sulfate; cumene hydroperoxide and N,N-dimethylaniline; or the like.

In some embodiments, the precursor composition includes only the polymerizable material, the polar solvent, and an initiator such as a photoinitiator. In most embodiments, the initiator is present in an amount no greater than 4 weight percent, no greater than 3 weight percent, no greater than 2 weight percent, no greater than 1 weight percent, or no greater than 0.5 weight percent based on the total weight of the precursor composition.

The precursor composition can include one or more optional active agents. The active agent provides some added functionality to the shaped polymeric material. The shaped polymeric material functions as a carrier for the active agent. If present, the active agents are usually present in an amount no greater than 30 weight percent, no greater than 25 weight percent, no greater than 20 weight percent, no greater than 15 weight percent, no greater than 10 weight percent, or no greater than 5 weight percent based on the total weight of the precursor composition.

In some embodiments, the active agent can migrate into and out of the shaped polymeric material. In other embodiments, the active agent tends to be stationary and remain within the shaped polymeric material. For example, the molecular size of the active agent may prevent elution or diffusion of the active agent out of the shaped polymeric material. In another embodiment, the active agent may be attached to the shaped polymeric material with a covalent or ionic bond. Active agents optionally can have one or more ethylenically unsaturated groups that can react with other ethylenically unsaturated groups to become part of the polymerizable material or to become attached to the polymeric material of the shaped polymeric material.

Some active agents are biologically active agents. As used herein, the terms "biologically active agent" and "bioactive agent" are used interchangeably and refer to a compound or mixture of compounds that has some known effect on living systems such as, for example, a bacteria or other microorganisms, plant, fish, insect, or mammal. The bioactive agent is added for the purpose of affecting the living system such as affecting the metabolism of the living system. Examples of bioactive agents include, but are not limited to, medicaments, herbicides, insecticides, antimicrobial agents, disinfectants and antiseptic agents, local anesthetics, astringents, antifungal agents, antibacterial agents, growth factors, vitamins, herbal extracts, antioxidants, steroids or other anti-inflammatory agents, compounds that promote wound healing, vasodilators, exfoliants such as alpha-hydroxy acids or beta-hydroxy acids, enzymes, nutrients, proteins, and carbohydrates. Still other bioactive agents include artificial tanning agents, tanning accelerants, skin soothing agents, skin tightening agents, anti-wrinkle agents, skin repair agents, sebum inhibiting agents, sebum stimulators, protease inhibitors, anti-itch ingredients, agents for inhibiting hair growth, agents for accelerating hair growth, skin sensates, anti-acne treatments, depilating agents, hair removers, corn removers, callus removers, wart removers, sunscreen agents, insect repellants, deodorants and antiperspirants, hair colorants, bleaching agents, and anti-dandruff agents. Any other suitable bioactive agent known in the art can be used.

Other active agents are not biologically active. These active agents are added to provide some non-biological functionality to the shaped polymeric material. That is, these active agents are not added for the purpose of affecting a living system such as affecting the metabolism of the living system. Suitable active agents, for example, can be selected to alter the odor, charge, color, density, pH, osmolarity, water activity, ionic strength, or refractive index of the shaped polymeric material. The active agent can also be selected to provide a reactive group or compound. Examples of non-biologically active agents include emulsifiers or surfactants (including anionic surfactants, cationic surfactants, zwitterionic surfactants, non-ionic surfactants, and combinations thereof), pigments, inorganic oxides (such as silicon dioxide, titania, alumina, and zirconia), fragrances such as aromatherapy agents and perfumes, odor absorbing agents, humectants, lubricants, dyes, bleaching or coloring agents, flavorings, decorative agents such as glitter, emollients, acids, bases, buffers, indicators, soluble salts, chelating agents, and the like. Some humectants that are liquids at room temperature that are miscible with water (e.g., glycols and other polyols) in the amounts used are considered to be part of the polar solvent when the precursor composition of the swollen shaped polymeric material or dried shaped polymeric material is calculated.

In some embodiments, the active agent is an indicator. Any suitable chemistry can be used for the indicator. The indicator can detect, for example, a specific pH range or the presence of a specific class of compounds. The presence of some specific classes of compounds can result in a color change. Ninhydrin, for example, can be used to detect the presence of a protein or amino group. The indicator can also be a typical pH indicator such as methyl blue or phenolphthalein.

Inorganic oxides nanoparticles can be added to the shaped polymeric material to increase the refractive index of the shaped polymeric material. For example, the shaped polymeric material can be loaded with zirconia nanoparticles or titania nanoparticles. Zirconia nanoparticles can be prepared using the methods described, for example, in U.S. Pat. No. 6,376,590 (Kolb et al.) and U.S. Patent Publication No. 2006/0148950A1 (Davidson et al.).

Any of the active agents may have a polymerizable group. The polymerizable group on the active agent can be used to prevent the migration of the active agent out of the shaped polymeric material. Cationic monomers having an ethylenically unsaturated group as well as a quaternary amino group may function as an antimicrobial agent and can be included in the polymerizable material of the precursor composition. The cationic monomer is often a (meth)acrylate having a quaternary amino group.

In some instances, shaped polymeric materials can have unreacted polymerizable groups. The unreacted polymerizable groups of the shaped polymeric materials may be reacted post-formation with active agents having polymerizable groups. For example, a cationic monomer having an ethylenically unsaturated group and a quaternary amino group can be reacted with the shaped polymeric material having unreacted ethylenically unsaturated groups. A mixture containing the shaped polymeric material, the cationic monomer, and a photoinitiator can be exposed to actinic radiation to react the ethylenically unsaturated group of the cationic monomer with an unreacted ethylenically unsaturated group of the shaped polymeric material. The reaction product is a shaped polymeric material with attached quaternary amino groups.

The shaped polymeric material can be formed in a mold having at least two separate wells. A mold is provided to define the size and shape of the shaped polymeric material. A precursor composition is added and retained within the wells of the mold. The precursor composition is then exposed to radiation to at least partially polymerize the polymerizable material. The at least partially polymerized material within the wells forms a first swollen shaped polymerizable material.

A mold may be a film, a sheet, a web, a belt, a roller, a drum, a ribbon, discrete particles or other three dimensional shapes or structures, or combinations thereof for which a flowable or partially flowable material, such as a precursor composition, can be applied. The mold can be formed from a polymeric material, a metallic material, a ceramic material or a combination thereof. The material selected for the mold generally has properties suitable for a particular application. Some properties to consider in forming a mold include physical, chemical, optical, electrical, and thermal properties.

A mold can be formed having features on its surfaces. These features can be transferred from the mold to a flowable or partially flowable material applied or coated onto the mold. The surfaces of the mold may be smooth, partially smooth, textured, or a combination thereof. Examples of textured or structured surfaces comprising nano-, micro-, and macro-replicated features and patterns are described in U.S. Pat. No. 6,649,249 (Engle et al.) and U.S. Pat. No. 7,105,809 (Wood et al.). The mold may further include structured surfaces having regular or random features spatially located throughout the surface.

Molds further include features commonly known as wells. Wells may be referred to as cavities, regions, pockets, ridges, channels and the like. The well provides a location on a surface for retaining a flowable or partially flowable material. Wells generally have volumes with dimensions such as diameter, radius, height, width and length. The material in the wells can be retained by walls and/or other features located on or within the mold. In one embodiment, the wells can be located within a structured surface of a mold. The wells of the mold can be located separately from each other with a land (e.g., region) separating the wells.

Wells may have different shapes. Examples of shapes of the wells may include conical, cubic, triangular, rectangular, pyramidal, and other shapes suitable for retaining a volume of a material. The base of the well refers to a location within the well generally spaced a distance from the top of the well. The top of the well may refer to a land or a surface to distinguish individual wells from one another. In a mold having at least two separate wells, a first well may have the same shape as a second well. In another mold, the first well may have a different shape than the second well.

Similarly, the wells can have random, partially random, or precisely spaced features positioned on the walls of the well, on the land areas, and within the wells. Some of these features may include protrusions and depressions. These features are commonly referred to as topographical features.

Some examples of topographical features of wells range from the extreme of cubic wells with parallel vertical, planar walls to the extreme of hemispherical wells, with any possible solid geometrical configuration of walls between those extremes. Other example topographies or topographical features include conical wells with angular, planar walls, truncated pyramid wells with angular, planar walls, and cube corner shaped wells.

Some of the topographical features in the wells, or in the wells themselves may be formed on a nano-, micro- or macro-scale. Similarly, some of the topographical features may be found on the mold or at least on the land areas between the wells. The dimensions of these features may be limited to the tooling or equipment for manufacturing the features. Generally, a mold having a microstructured surface, for example, may have a desired topography on at least one surface. These microstructures include a configuration of features such that at least two dimensions of the features are microscopic. Microscopic features are sufficiently small so as to require an optic aid to the naked eye to determine their shape. The dimensions of the topographical features range from about two hundred micrometers or less in at least two of the three possible dimensions (in/out of the plane of the mold, and in each direction along the plane of the mold). The topographical features have a desired characteristic size (such as length measured along any dimension) and feature density (features per unit area of mold surface). A feature, as described earlier can be anything that represents a departure or deviation from a flat planar surface. Some of the features can include those that protrude (nodules, posts, lumps, ridges), or those which are recessed (hoes, pits, fissures, crevices). Microstructured surfaces may also possess a combination of protruding and recessed features (e.g., furrows and ridges, protruding and recessed pyramids). In the case of ridges, furrows, or intersecting planes, a feature may be a corner or linear intersection of such ridges, furrows, or planes.

A feature may be such that its characteristic length is in all three dimensions (i.e., into and out of the plane of the film, and in each orthogonal direction along the plane of the film) is similar. Conversely, a feature may be such that the characteristic length in one or more directions is somewhat longer, or even much longer, than in the other directions (i.e., in the case of features such as ridges or furrows).

In some embodiments, the microstructured features include those possessing a maximum characteristic length in one or more directions of two hundred micrometers. In some embodiments, the maximum characteristic length is fifty micrometers, and in another embodiment, the characteristic length is less than 10 micrometers. In some embodiments, the minimum characteristic length in one or more directions is one nanometer. In other, the minimum characteristic length is ten nanometers, and in another embodiment the minimum characteristic length is one hundred nanometers. Also, in some embodiments, microstructured feature densities in a mold can be in a range of 100 features or greater per square millimeter ($mm^2$). In some embodiments, the mold may have a density of greater than 1,000 features or greater per $mm^2$, and in other embodiments, a density of greater of than 10,000 features or greater per $mm^2$. FIG. 1 illustrates a mold having at least two separate wells, and features located within the wells.

In some embodiments, features may be present on a regular repeating basis, or they may be random. In other embodiments, the features may be present over the entire area of the mold, or they may be present only in areas such as the wells or optionally on the land areas, in which the flowable or partially flowable material is to be deposited.

At least two separate wells of the mold can be used to retain a flowable or partially flowable material such as a precursor composition. The precursor composition is generally a liquid composition consisting of curable, polymerizable or crosslinkable molecules, which are cured while in contact with the mold. The precursor composition generally has a viscosity sufficient for flowing and adding the composition into the at least two separate wells of the mold.

The precursor composition can be positioned in at least a portion of at least two separate wells of the mold by different methods. Some of the positioning or addition methods include, but are not limited to, gravity filling, pressure filling, or vacuum filling. In one example, the precursor composition may be positioned in at least a portion of the wells by capillary action. The precursor composition may be positioned in at least a portion of the wells, such that the precursor composition is positioned in at least 5 percent of the volume of the at least two separate wells. In some embodiments, the precursor composition may be positioned in at least 15 percent, in at least 25 percent, or at least 35 percent of the volume of the at least two separate wells. The precursor composition may be positioned up to 100 percent, up to 90 percent, up to 80 percent, or up to 70 percent of the volume of the at least two separate wells. The precursor composition may be positioned in at least a portion of the at least two separate wells in a range of 5 to 100 percent, 15 to 90 percent, 25 to 80 percent, or 35 to 70 percent of the volume of the at least two separate wells.

In some embodiments, the precursor composition may be positioned to fill in excess of 100 percent of the volume of the at least two separate wells. At this volume, the precursor composition may cover the land areas between the wells providing for connection between the two separate wells. The shaped polymeric material may be in the form of a film or sheet having the polymerizable material of the wells attached to the film or sheet.

After positioning the precursor composition in the wells of the mold, the precursor composition may be at least partially solidified by exposing the precursor composition to radiation within the two separate wells. The radiation at least partially polymerizes the polymerizable material, which has an average number of ethylenically unsaturated groups per monomer molecule equal to at least 1.2. The polymerizable material polymerizes by a free-radical polymerization process. The polymerized material assumes the shape and features within the two separate wells of the mold. Most of the features within the wells or on the microstructured surface of the mold will be the negative image of the features designed or displayed on a shaped polymeric material. For example, ridges having wells on the surface of the mold will manifest as channels on a surface of the shaped polymeric material.

The radiation used to polymerize the polymerizable material can be referred to as actinic radiation (e.g., radiation having a wavelength in the ultraviolet or visible region of the spectrum), accelerated particles (e.g., electron beam radiation), thermal (e.g., heat or infrared radiation), or the like. The radiation is often actinic radiation or accelerated particles, because these energy sources tend to provide good control over the initiation and rate of polymerization. Additionally, actinic radiation and accelerated particles can be used for curing at relatively low temperatures. This avoids degrading components that might be sensitive to the relatively high temperatures that might be required to initiate the polymerization reaction with thermal radiation. Any suitable actinic radiation sources that can produce energy in the desired region of the electromagnetic spectrum can be used. Exemplary sources of actinic radiation include mercury lamps, xenon lamps, carbon arc lamps, tungsten filament lamps, lasers, sunlight, light emitting devices (LED) and the like.

The radiation source may be a single radiation source or a plurality of radiation sources that are the same or different. The radiation source provides energy such as infrared radiation, visible radiation, ultraviolet radiation, electron beam radiation, microwave radiation, or radio frequency radiation. The particular energy source used will depend upon the particular precursor composition. Suitable non-ionizing radiation sources include continuous and pulsed sources and may be broadband or narrowband sources such as monochromatic sources. Exemplary non-ionizing radiation sources include, but are not limited to, mercury lamps (such as low, medium, and high-pressure versions as well as their additive or doped versions), fluorescent lamps, germicidal lamps, metal halide lamps, halogen lamps, light emitting diodes, lasers, excimer lamps, pulsed xenon lamps, tungsten lamps, and incandescent lamps. Infrared radiation sources and microwave radiation sources may be used, as well as ionizing radiation sources such as electron beams. A combination of radiation sources may also be used.

In some exemplary methods, electromagnetic radiation having a wavelength in the range of 100 to 1000 nanometers (nm), 100 to 800 nanometers, or 100 to 700 nanometers can be used. In some methods, ultraviolet radiation having a wavelength in the range of 100 to 400 nanometers or 200 to 400 nanometers can be used. Ultraviolet radiation at wavelengths below 200 nanometers from excimer sources, for example, can be used. In some embodiments, the radiation source is a high-radiance ultraviolet source, such as a medium-pressure mercury lamp of at least 100 W/inch (40 W/cm). Low-radiance lamps, including low-pressure mercury lamps such as germicidal lamps, can also be used.

The precursor composition may be exposed to radiation for a time generally no more than 30 seconds, no more than 15 seconds, no more than 10 seconds, no more than 5 seconds, no more than 3 seconds, no more than 2 second, no more than 1 second or no more than 0.5 seconds. Upon exposure to radiation, the polymerizable material can at least partially polymerize to form a swollen shaped polymeric material. The polymerizable material may crosslink or the polymer chains may propagate during exposure to radiation.

The shaped polymeric materials are formed by subjecting the precursor composition to radiation within the wells resulting in the free-radical polymerization of the polymerizable material. The polymerized polymeric material assumes the shape of the wells of the mold. Because the precursor composition includes polar solvent in addition to the polymerizable material, the shaped polymeric materials are swollen with the polar solvent. The shaped polymeric materials can be described as a first swollen shaped polymeric material, a hydrogel shaped polymeric material, a shaped polymeric material swollen with solvent, or a swollen shaped polymeric material. All these terms may be used interchangeably herein.

The polymeric material in the swollen shaped polymeric material is generally crosslinked, but it may contain some unreacted polymerizable or reactive groups. The unreacted polymerizable groups typically include ethylenically unsaturated groups capable of further free-radical reactions. Other types of polymerizable groups such as hydroxyl groups or amino groups can be present that are capable of condensation reactions or nucleophilic substitution reactions.

Figure 2:
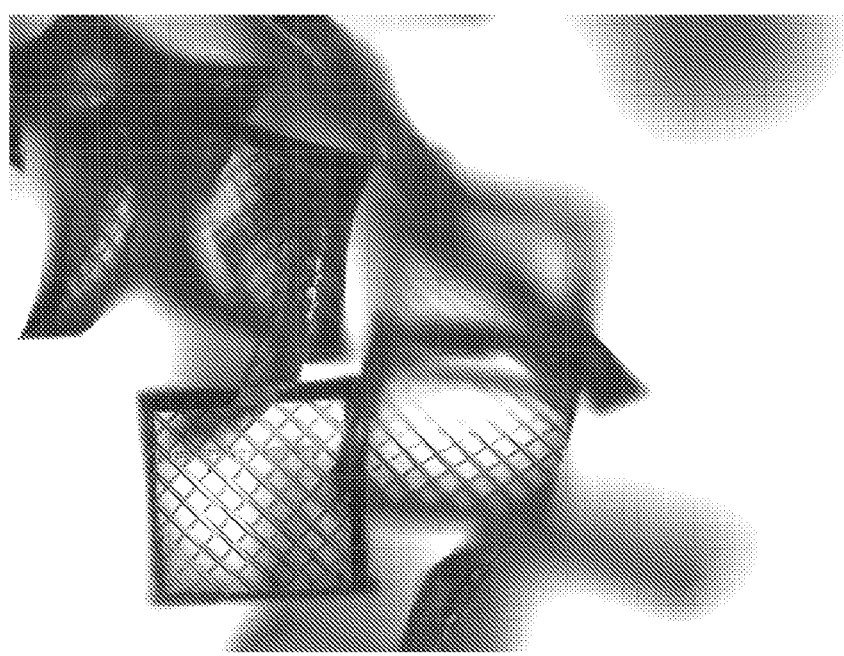
FIG. 2 is an optical micrograph of shaped polymeric materials of Example 1.

FIG. 2 illustrates a swollen shaped polymeric material formed in Example 1. The swollen shaped polymeric material contains the inverse topography of the mold having at least two separate wells represented in FIG. 1.

In some embodiments, the swollen shaped polymeric materials can also contain an active agent. Active agents can be present in the precursor composition used to prepare the swollen shaped polymeric material. Alternatively, the swollen shaped polymeric materials can be dried and swollen a second time with a sorbate. That is, the dried shaped polymeric material can sorb the sorbate to form a second swollen shaped polymeric material. The sorbate often includes an active agent. The active agent can be a biologically active agent, a non-biologically active agent, or a mixture thereof. Suitable active agents are described above.

When included in the precursor composition, the active agents are preferably stable and/or resistant to the radiation used to polymerize the material. Active agents that are not stable or resistant to radiation may fare better if added after formation of the shaped polymeric material (i.e., the shaped polymeric material can be dried and then exposed to a sorbate that includes the active agent). Unlike the active agents that often can be added either to the precursor composition or after formation of the shaped polymeric material, the processing agents are typically included in the precursor composition.

The amount of the active agent can be in the range of 0 to 70 weight percent based on the weight of the swollen shaped polymeric material. In some exemplary swollen shaped polymeric materials, the amount of the active agent is no greater than 50 weight percent, 40 weight percent, 30 weight percent, 20 weight percent, 10 weight percent, 5 weight percent, 2.5 weight percent, or no greater than 1 weight percent of the swollen shaped polymeric materials.

Some exemplary swollen shaped polymeric materials may contain no greater than 90 weight percent polymeric material, at least 10 weight percent polar solvent, and 0 to 30 weight percent active agent based on a total weight of the swollen shaped polymeric materials.

The swollen shaped polymeric materials are generally homogeneous and typically do not contain discernible features other than those made imparted by the mold. Development of channels or features on the swollen shaped polymeric materials may result from surfaces of the well. The polymeric matrix, which includes the polar solvent and polymeric material, is usually present as a single phase in the swollen shaped polymeric material, with no discernible boundary between the solvent and the polymeric material. If an active agent is present, however, the active agent may or may not be distributed homogeneously throughout the shaped polymeric material. Further, the active agent may be present in a separate phase from the polymeric matrix.

Generally, the homogeneity of the shaped polymeric materials (i.e., without an active agent) are characterized by having no discernible porosity or voids when viewed under a microscope such as an environmental scanning electron microscope with magnification up to 50 times. The shaped polymeric materials often have no discernible porosity or voids when viewed under a field emission scanning electron microscope with a magnification up to 50,000 times.

Swollen shaped polymeric materials are often prepared without the use of opaque components that might scatter light. These materials can be clear or transparent, with little or no opacity or haziness. In some embodiments, swollen shaped polymeric materials that are clear are preferred. In other embodiments, clarity may not be required and various components can be added that may affect the appearance of the shaped polymeric materials.

The term "transparent" as used in reference to the shaped polymeric materials, means that the shaped polymeric materials do not show significant scatter of visible light in an amount that can be visually detected. In some embodiments, air or other gases may be entrained in the shaped polymeric materials. Air or other gases can create opacity at the phase boundaries; however, this is not phase-separation of the polymeric material in the polar solvent. Shaped polymeric materials are considered transparent if a colorless, virtually void-free cured film having a thickness of 250 micrometers containing smooth or flat parallel faces (i.e., patternless) has a transmission of at least 85 percent at a wavelength of 550 nanometers. In some embodiments, at least 88 percent, at least 90 percent, at least 95 percent of light having a wavelength of 550 nanometers is transmitted through the shaped polymeric material.

The haze or opacity can be characterized using a haze meter, such as a BYK-Gardner Hazegard Plus hazemeter, which has a broadband light source. The transmittance through shaped polymeric material can be at least 85 percent, at least 88 percent, at least 90 percent, or at least 95 percent with haze being less than 15 percent, less than 12 percent, less than 10 percent, or less than 5 percent. Haziness, in many embodiments, is indicative of phase-separation.

The shaped polymeric materials may be rigid or elastomeric and may or may not be easily crushed (e.g., friable). A higher content of polymeric material tends to increase the modulus and crush strength of the shaped polymeric material. A greater amount of crosslinking achieved by using a precursor composition with a higher average functionality also tends to increase the modulus and crush strength of the shaped polymeric materials. The average functionality refers to the average number of polymerizable groups (ethylenically unsaturated groups) per monomer molecule.

The shaped polymeric materials can have a wide variety of sizes. The dimensions of the shaped polymeric materials depends on the size of the wells (including the features on the surfaces of the wells) within the mold used to generate the shapes of the precursor composition prior to radiation curing can be of any size. In some embodiments, the dimensions of the shaped polymeric materials can range from less than one micrometer to several thousand micrometers or more. In other embodiments, particularly suitable dimensions, such as the height or depth of the shaped polymeric materials are in the range of 0.5 to about 5000 micrometers, in the range of 1 to 1000 micrometers, in the range of 10 to 1000 micrometers, or in the range of 100 to 1000 micrometers. The length or widths of the shaped polymeric materials are in the range of 0.5 to 5000 micrometers, in the range of 1 to 1000 micrometers, or in the range of 100 to 1000 micrometers.

After exposing the precursor composition to radiation, the polymerizable material is at least partially polymerized to form a first swollen shaped polymeric material. The first swollen shaped polymeric material can be removed from the mold. The swollen shaped polymeric material generally has the dimensions of the well of the mold. Conventionally, the shaped polymeric material can be removed from the mold by gravity or vibratory techniques.

In one embodiment, the first swollen shaped polymeric material can be removed by applying a polar solvent. The polar solvent (e.g., water) may be applied to the swollen shaped polymeric material such that the swollen shaped polymeric material releases out of the mold. The polar solvent may change the dimensions of the shaped polymeric material (e.g., swelling) such that the shaped polymeric material lifts or squeezes out of the well of the mold. After exiting the well, the swollen shaped polymeric materials can retain the inverse features shown in the wells of FIG. 2.

In some embodiments of the shaped polymeric material and the methods of making the shaped polymeric material, at least a portion of the polar solvent can be removed from the first swollen shaped polymeric material to form a dried shaped polymeric material. The dried shaped polymeric material can then be contacted with a sorbate for a time sufficient for the dried shaped polymeric material to sorb at least a portion of the sorbate. That is, a first swollen shaped polymeric material can be dried to form a dried shaped polymeric material that can then be contacted with a sorbate to form a second swollen shaped polymeric material. The sorbate can contain at least one active agent. In addition to the active agent, the sorbate can include a fluid such as a liquid or a supercritical fluid. Some exemplary sorbates include an active agent plus a polar solvent.

As used herein, the term "sorb" refers to adsorb, absorb, or a combination thereof. Likewise, the term "sorption" refers to adsorption, absorption, or a combination thereof. The sorption can be a chemical process (i.e., a chemical reaction occurs), a physical process (i.e., no chemical reaction occurs), or both. The term "sorbate" refers to a composition that can be sorbed by shaped polymeric materials such as dried shaped polymeric materials.

More specifically, a method of making a shaped polymeric material that includes an active agent is provided. The method includes forming a precursor composition containing (a) a polar solvent and (b) polymerizable material that forms a single phase with the polar solvent. The polymerizable material is capable of free-radical polymerization and has an average number of ethylenically unsaturated groups per monomer molecule greater than 1.2. The method further includes adding a portion of the precursor composition to a mold having at least two separate wells, wherein the precursor composition is retained within the wells. The precursor composition is positioned in at least a portion of the two separate wells. The precursor composition within the wells is exposed to radiation for a time sufficient to at least partially polymerize the polymerizable material and to form a first swollen shaped polymeric material. The method further includes removing at least a portion of the polar solvent from the first swollen shaped polymeric material to form a dried shaped polymeric material. The dried shaped polymeric material is then contacted with a sorbate for a time sufficient for the dried shaped polymeric material to sorb at least a portion of the sorbate and to form a second swollen shaped polymeric material. The sorbate typically contains an active agent.

The amount of polar solvent removed from the first swollen shaped polymeric material to form a dried shaped polymeric material can be any amount desired up to the amount present in the original precursor composition. The dried shaped polymeric material often contains at least a small amount of polar solvent remaining in the shaped polymeric material. Additionally, if the shaped polymeric material will be contacted with a sorbate to sorb an active agent into or onto the shaped polymeric materials, the amount of polar solvent present in the dried shaped polymeric material is generally no more than 25 weight percent based on the weight of the dried shaped polymeric material. The amount of polar solvent in the dried shaped polymeric material can be less than 20 weight percent, less than 15 weight percent, less than 10 weight percent, less than 5 weight percent, less than 2 weight percent, or less than 1 weight percent of the weight of the dried polymeric shaped polymeric material. Generally, the more solvent removed from the first swollen shaped polymeric material, the greater is the amount of the sorbate that can be sorbed by the dried shaped polymeric material.

The first swollen shaped polymeric material shrinks when the polar solvent is removed and may resemble collapsed, deformed or deflated shapes based on the wells of the mold; some of the dried shaped polymeric materials may have different shapes when viewed in the cross-section. The cross-sectional shape of the dried shaped polymeric material will depend on the cross-sectional shape of the first swollen shaped polymeric material. The amount of shrinkage depends on the volume of polar solvent initially present in the first swollen shaped polymeric material and the extent to which it is removed by drying. The shaped polymeric materials may experience shrinking in all three dimensions separately or uniformly.

The dried shaped polymeric material (particularly in the absence of an active agent or other insoluble additives) generally remains homogeneous and does not contain macroscopic (i.e., greater than 100 nm) internal pores or channels. Generally, the shaped polymeric materials have no discernible porosity or voids when viewed under a microscope. Typically, there are no discernible pores when the shaped polymeric materials are viewed using environmental scanning electron microscopy with magnification up to 50 times. Some shaped polymeric materials have no discernible pores when viewed using field emission scanning electron microscopy with magnification up to 50,000 times. The dried shaped polymeric materials may have high modulus, high crush strength, or a combination thereof. These properties can be similar to or greater than those of the swollen shaped polymeric material.

A swollen shaped polymeric material can be dried (i.e., the swollen shaped polymeric material can have at least a portion of the polar solvent removed) by any of a variety of methods including heating in a conventional oven such as a convection oven, heating in a microwave oven, air-drying, freeze-drying, or vacuum-drying. The optimal method for drying a given shaped polymeric material composition is dependent on the identity and amount of the polar solvent present in the swollen shaped polymeric material as well as the heat stability of components in the shaped polymeric material such as bioactive agents. When water is present, preferred drying methods include conventional ovens such as convection ovens, microwave ovens, vacuum ovens, and freeze-drying. For water, suitable temperatures for drying at atmospheric pressure are often close to or exceeding 100° C. In some cases it may be desirable to heat the dried shaped polymeric material to higher temperatures. This may improve the shaped polymeric material strength through condensation or other chemical reactions. For example, the shaped polymeric materials can be heated to greater than 140° C., greater than 160° C., or even greater than 180° C. The shaped polymeric material does not coalesce when dried to form, for example, a film or sheet. Rather, the dried shaped polymeric materials tend to remain as separate shaped polymeric materials.

The dried shaped polymeric material can be readily swollen again, for example, by impregnating with a sorbate, back to its swollen state that can approximate the original size. Typically, the volume of sorbate that can be sorbed by the dried shaped polymeric material to form a second swollen polymeric shaped polymeric material is nearly equal to the volume of polar solvent and other non-polymerized components removed from the first swollen shaped polymeric material during the drying process. In cases where the polar solvent present in the precursor composition and in the resulting first swollen shaped polymeric material is different than the solvent in the sorbate used to swell the shaped polymeric material a second time (e.g., swell a dried shaped polymeric material), the dried shaped polymeric material may swell very little or may swell beyond its original, as polymerized, dimensions. For example, a sorbate comprising a non-polar solvent may take a day or a period of time longer than a day to re-swell the dried shaped polymeric material to its final size.

Dried shaped polymeric materials can be loaded with an active agent, especially those that are sensitive to the heat or radiation encountered during the formation of the swollen shaped polymeric materials such as medicaments, pharmaceuticals, insecticides, herbicides, dyes, fragrances, or mixtures thereof. To provide a shaped polymeric material with an active agent, the dried shaped polymeric material is contacted with a sorbate that contains the active agent. If the active agent is not a liquid, the sorbate typically also contains a fluid such as a polar solvent or supercritical fluid (e.g., carbon dioxide). The sorbate can be a solution, suspension, emulsion (e.g., macro emulsion, microemulsion, or a nanoemulsion) or dispersion. In many embodiments, the sorbate is a solution. The dried shaped polymeric material typically sorbs at least a portion of the sorbate. Exposure of the dried shaped polymeric material to the sorbate results in the impregnation of the shaped polymeric material with an active agent.

The sorbate often includes the active agent and a liquid such as a polar solvent. Sorption of the liquid often causes the shaped polymeric material to swell. The liquid typically facilitates the transport of the active agent into the shaped polymeric material. The liquid will often carry the active agent throughout the shaped polymeric material to form a homogenous swollen shaped polymeric material. In some embodiments, however, the active agent may remain on the surface of the shaped polymeric material or there may be a gradient of the active agent throughout the shaped polymeric material with a higher concentration on the surface. For example, the size of the active agent (e.g., molecular size), its charge relative to the shaped polymeric material, as well as the polar solvent composition may affect the migration (e.g., diffusion) of the active agent into the dried shaped polymeric material.

The dried shaped polymeric material can often sorb an amount of sorbate that is equal to at least 10 weight percent, at least 20 weight percent, at least 40 weight percent, at least 50 weight percent, at least 60 weight percent, at least 80 weight percent, at least 100 weight percent, at least 120 weight percent, at least 140 weight percent, at least 160 weight percent, at least 180 weight percent, or at least 200 weight percent based on the weight of the dried shaped polymeric materials. In some embodiments, the weight increase is less than 300 weight percent, less than 275 weight percent, or less than 250 weight percent based on the weight of the dried shaped polymeric materials.

The shaped polymeric materials can be a carrier for an active agent, which can be present in at least a portion of the interior of the shaped polymeric material or on at least a portion of the surface of the shaped polymeric material. The active agent can be included in the precursor composition used to form the shaped polymeric material. Alternatively, the active agent can be sorbed by a shaped polymeric material that has been at least partially dried. The shaped polymeric material can provide diffusion-controlled transport of the active agent both into and from the bulk. That is, in many embodiments, the active agent can diffuse into the shaped polymeric material, diffuse out of the shaped polymeric material, or both. The rate of diffusion can be controlled by, for example, varying the polymeric material and the crosslink density, by varying the polar solvent, by varying the solubility of the active agent in the polar solvent, and by varying the molecular weight of the active agent. The diffusion can take place over a period of several hours, several days, several weeks, or several months.

In some applications, it may be desirable that the shaped polymeric material containing the active agent is in a dry state. After the addition of the active agent by exposing the dried shaped polymeric material to the sorbate to form a second swollen shaped polymeric material that contains the active agent, the second swollen shaped polymeric material can be dried again. When this dried shaped polymeric material is exposed to moisture, the active agent can diffuse from the shaped polymeric material. The active agent can remain dormant in the shaped polymeric material until exposed to moisture. That is, the active agent can be stored within the dry shaped polymeric material until the shaped polymeric material is exposed to moisture. This can prevent the waste or loss of the active agent when not needed and can improve the stability of many moisture sensitive active agents that may degrade by hydrolysis, oxidation, or other mechanisms. Potential applications taking advantage of the diffusion controlled uptake or delivery of the active agent include, for example, drug delivery, wound management, and sustained-released antibacterial and antifungal protection, air freshening agents, time-released insecticides, and time-released attractants for higher animals such as fish or mammals.

In some embodiments, the shaped polymeric materials can be exposed to the sorbate, dried to form a dried shaped polymeric material, and re-exposed to moisture again. The shaped polymeric materials may be regenerated multiple times by the steps of sorbing and drying. The shaped polymeric materials may be regenerated multiple times with the sorbate. In another embodiment, shaped polymeric materials containing a first active agent may be exposed to a concentrated solution of a second active agent or other material. The second active agent may sorb into shaped polymeric materials to form shaped polymeric materials having more than one active agent. The second active agent may sorb into the shaped polymeric material to the exclusion of the first agent from the shaped polymeric materials. A combination of active agents may be sorbed by the shaped polymeric materials, and optionally dried.

As wound dressings, the shaped polymeric materials can be loaded with various active agents that provide a therapeutic function. Wound dressings containing these active agents may reduce or eliminate infection of the wound. In addition, these wound dressings can speed the rate of wound healing when therapeutic active agents such as anti-inflammatory drugs, growth factors, alpha-hydroxyacids, enzyme inhibitors such as matrix metalloproteinase (MMP) inhibitors, enzyme activators, vasodilaters, chemotactic agents, hemostatic agents (e.g., thrombin), antimicrobial agents, antihistamines, antitoxins, anesthetics, analgesics, vitamins, nutrients, or combinations are added to the shaped polymeric materials. When used in wound dressings, the shaped polymeric materials are typically dry prior to use in highly exuding wounds but may be used swollen to add moisture to dry wounds.

In some embodiments, the swollen shaped polymeric material can be used to deliver antimicrobial agents to either mammalian tissue or another environment outside of the shaped polymeric materials. Some exemplary antimicrobial agents that can be added to the shaped polymeric material include iodine and its various complexed forms, which are commonly referred to as iodophors. Iodophors are complexes of elemental iodine or other iodine species (e.g., triodide) with certain carriers. Iodophors can be formed between elemental iodine or other iodine species, and the polymer matrix itself. For example, a carrier such as polyethylene glycol is known. These iodophors function by not only increasing the iodine solubility but by reducing the level of free molecular iodine in solution and by providing a type of sustained release reservoir of iodine. Iodophors can be formed using polymeric carriers such as polyvinylpyrrolidone (PVP); copolymers of N-vinyl lactams with other unsaturated monomers such as, but not limited to, acrylates and acrylamides; various polyether glycols (PEGs) including polyether-containing surfactants such as nonylphenolethoxylates and the like; polyvinyl alcohols; polycarboxylic acids such as polyacrylic acid; polyacrylamides; and polysaccharides such as dextrose. Other suitable iodophors include the protonated amine oxide surfactant-triiodide complexes described in U.S. Pat. No. 4,597,975 (Woodward et al.). In some applications, the iodophor is povidone-iodine. This can be obtained commercially as povidone-iodine USP, which is a complex of K30 polyvinylpyrrolidone and iodide wherein the available iodine is present at about 9 weight percent to about 12 weight percent.

In some embodiments, various combinations of antimicrobial agents can be used in the precursor composition or sorbate. Any other known antimicrobial agents that are compatible with the precursor compositions or the resulting shaped polymeric materials can be used. These include, but are not limited to, chlorhexidine salts such as chlorhexidine gluconate (CHG), parachlorometaxylenol (PCMX), triclosan, hexachlorophene, fatty acid monoesters and monoethers of glycerin and propylene glycol such as glycerol monolaurate, glycerol monocaprylate, glycerol monocaprate, propylene glycol monolaurate, propylene glycol monocaprylate, propylene glycol moncaprate, phenols, surfactants and polymers that include a ($C_{12}$-$C_{22}$) hydrophobe and a quaternary ammonium group or a protonated tertiary amino group, quaternary amino-containing compounds such as quaternary silanes and polyquaternary amines such as polyhexamethylene biguanide, silver containing compounds such as silver metal, silver salts such as silver chloride, silver oxide and silver sulfadiazine, methyl parabens, ethyl parabens, propyl parabens, butyl parabens, octenidene, 2-bromo-2-nitropropane-1,3 diol, or mixtures thereof. Other antimicrobial agents are described in U.S. Patent Application Publication Nos. 2006/0052452 (Scholz et al.), 2006/0051385 (Scholz et al.), and 2006/0051384 (Scholz et al.).

In some embodiments, antimicrobial agents having limited solubility in polar solvents can be dissolved in volative solvents, and subsequently sorbed by the shaped polymeric materials. The volative solvent can then be removed by evaporation.

In some embodiments, active agents can be sorbed into the shaped polymeric materials to deliver any of the aforementioned active agents to the skin for transdermal delivery into the dermis. One example for transdermal delivery includes a patch format, which is similar to a wound dressing. The shaped polymeric materials comprising active agents may or may not be in direct contact with the skin, but may serve as a reservoir for the active agent.

Additionally, shaped polymeric materials can be used to concentrate various materials such as contaminants or toxins. For example, the shaped polymeric materials can be used to remove contaminants from water systems or ecosystems. By incorporation of various functionalities into the shaped polymeric material such as chelating agents, it may be possible to remove heavy metals, radioactive contaminants, and the like.

Shaped polymeric materials often contain unreacted ethylenically unsaturated groups. These ethylenically unsaturated groups can be reacted with other monomers, such as monomers in a coating composition. The shaped polymeric materials can be polymerized into the final coating. Further, some shaped polymeric materials have other functional groups that can be further reacted. For example, some of the poly(alkylene oxide(meth)acrylates) included in the precursor composition have hydroxy groups that can undergo various nucleophilic substitution reactions or condensation reactions.

Exemplary cosmetic and personal care applications, for which the shaped polymeric material compositions may be used include, but are not limited to, wound care products such as absorbent wound dressings and wound packing to absorb excess exudates; first aid dressings, hot/cold packs, baby products, such as baby shampoos, lotions, powders and creams; bath preparations, such as bath oils, tablets and salts, bubble baths, bath fragrances and bath capsules; eye makeup preparations, such as eyebrow pencils, eyeliners, eye shadows, eye lotions, eye makeup removers and mascaras; fragrance preparations, such as colognes and toilet waters, powders and sachets; noncoloring hair preparations, such as hair conditioners, hair spray, hair straighteners, permanent waves, rinses, shampoos, tonics, dressings and other grooming aids; color cosmetics; hair coloring preparations such as hair dyes, hair tints, hair shampoos, hair color sprays, hair lighteners and hair bleaches; makeup preparations such as face powders, foundations, leg and body paints, lipsticks, makeup bases, rouges and makeup fixatives; manicuring preparations such as basecoats and undercoats, cuticle softeners, nail creams and lotions, nail extenders, nail polishes and enamels, and nail polish and enamel removers; oral hygiene products such as dentifrices, mouthwashes, and sustained release periodontal products and buccal cavity products each for the prevention and treatment of gingivitis; personal cleanliness products, such as bath soaps and detergents, deodorants, douches and feminine hygiene products; shaving preparations such as aftershave lotions, beard softeners, men's talcum powders, shaving creams, shaving soap and pre-shave lotions; skin care preparations such as cleansing preparations, skin antiseptics, depilatories, face and neck cleansers, body and hand cleansers, foot powders and sprays, moisturizers, night preparations, paste masks, and skin fresheners; and suntan preparations such as suntan creams, gels and lotions, and indoor tanning preparations.

In some applications, the shaped polymeric material contains an indicator that can detect the presence or absence of another compound of interest. The indicator can be added either to the precursor composition or to the dried shaped polymeric material using a sorbate that contains the indicator and an optional fluid such as a polar solvent (e.g., water, dimethylformamide, or the like). The shaped polymeric materials can be contacted with samples that potentially contain the compound to be detected. The indicator can then change color if the sample contains the compound to be detected. If the indicator does not migrate out of the shaped polymeric material when exposed to the sample, the shaped polymeric material may change color. If the indicator migrates out of the material when exposed to the sample, the sample itself may change color.

More specifically, the shaped polymeric material can be loaded with an indicator such as ninhydrin that is capable of detecting the presence of amino-containing materials. The dried shaped polymeric materials, which often are clear and colorless, can be loaded with ninhydrin to form a shaped polymeric material that has a yellow color. A sorbate that contains the ninhydrin as well as a polar solvent can be used to add the active agent to the shaped polymeric material. Upon contact of the ninhydrin-containing shaped polymeric material with an amino-containing material, the ninhydrin changes from a yellow to vivid purple color. Depending on the relative rates of diffusion of the ninhydrin and the amino-containing materials, the shaped polymeric material can change color from yellow to purple or the ninhydrin can migrate out of the shaped polymeric material and alter the color of an amino-containing sample. For example, small amino-containing materials can diffuse into the ninhydrin-containing shaped polymeric material and change the color of the shaped polymeric materials from yellow to purple. However, relatively large proteins cannot diffuse into the shaped polymeric materials as easily as the ninhydrin can migrate out of the materials. The color of the sample containing the protein can change to a purple color while the shaped polymeric material may not change to a purple color. In some other examples that contain a mixture of amino-containing materials, both the shaped polymeric material and the amino-containing sample may change to a purple color.

Shaped polymeric material loaded with dyes can be used as saturation indicators. The dye-containing shaped polymeric material can be dried. When the shaped polymeric material is contacted with water, the dye can diffuse out of the shaped polymeric material and alter the color of the water. Alternatively, dyes can be incorporated that are colorless in the absence of water but turn colored when water is sorbed into the shaped polymeric material. For example, certain pH indicators such as phenolthalein are colorless when dry but will turn color when wet.

The disclosure will be further clarified by the following examples which are exemplary and not intended to limit the scope of the disclosure.

EXAMPLES

The present disclosure is more particularly described in the following examples that are intended as illustrations only, since numerous modifications and variations within the scope of the present disclosure will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Test Methods/Procedures

Zone of Inhibition Assay Method
*Staphylococcus aureus* (ATCC 6538) (American Type Culture Collection, Manassas, Va.), gram positive (+) testing.

An inoculum suspension was prepared that contained a concentration of approximately $1 \times 10^8$ colony forming units (CFU) per milliliter (ml) in Phosphate Buffered Saline (PBS) obtained from EMD Biosciences of Darmstadt, Germany, using a 0.5 McFarland Equivalence Turbidity Standard. A bacterial lawn (i.e., bacterial layer covering the surface of the plate) was prepared by dipping a sterile cotton applicator into the inoculum suspension and swabbing the dry surface of a Mueller Hinton II plate in three different directions. A shaped polymeric material suspension containing 1 gram of shaped polymeric material in 1 ml of PBS was formed. Ten microliters (10 µl) of the shaped polymeric material suspension (containing 0.01 g shaped polymeric material) was applied to each 6 mm paper disk to form a wetted paper disk. The wetted paper disks were used for each (Mueller Hinton II) plate. Three wetted paper disks were prepared for each sample, placed onto the inoculated plate of each media type, and pressed firmly against the agar with sterile forceps to ensure complete contact with the agar. The plates were incubated at 28° C.+/−1° C. for 24 hours. The area under and surrounding the disks was examined for bacterial growth and the diameter of the zone of inhibition was recorded.

*Pseudomonas aeruginosa* (ATCC 9027) (American Type Culture Collection, Manassas, Va.), gram negative (−) testing An inoculum suspension was prepared that contained a concentration of approximately $1 \times 10^8$ colony forming units (CFU) per milliliter in Phosphate Buffered Saline (PBS) obtained from EMD Biosciences of Darmstadt, Germany using a 0.5 McFarland Equivalence Turbidity Standard. A bacterial lawn (i.e., bacterial layer covering the surface of the plate) was prepared by dipping a sterile cotton applicator into the inoculum suspension and swabbing the dry surface of a Mueller Hinton II plate in three different directions. A shaped polymeric material suspension containing 1 gram of shaped polymeric material in 1 ml of PBS was formed. Ten microliters (10 μl) of the shaped polymeric material suspension (containing 0.01 g shaped polymeric material) was transferred to each 6 mm paper disk to form a wetted paper disk. The wetted paper disks were used for each (Mueller Hinton II) plate. Three wetted paper disks were prepared for each sample, placed onto the inoculated plate of each media type, and pressed firmly against the agar with sterile forceps to ensure complete contact with the agar. The plates were incubated at 28° C.+/−1° C. for 24 hours. The area under and surrounding the disks was examined for bacterial growth and the diameter of the zone of inhibition was recorded.

Example 1

A homogeneous precursor composition was prepared by combining and mixing 16 grams of a 20-mole ethyoxylated trimethylolpropane triacrylate ((TMPTA), SR-415 commercially available from Sartomer of Exeter, Pa.; 24 grams deionized water; and 0.32 grams IRGACURE 2959 photoinitiator commercially available from CIBA Specialty Chemicals, Tarrytown, N.Y., in a container. The average functionality of the ethoxylated TMPTA used in this example and all subsequent examples was determined from HPLC data showing that the monomer was 53.6 weight percent trifunctional acrylate (52.5 mole percent), 45.3 weight percent difunctional acrylate (46.5 mole percent), and 1.0 weight percent monofunctional acrylate (1.1 mole percent). Using this information and assuming an average of 20-mole ethoxylation for each species, the average functionality was calculated to be about 2.5. The precursor composition was heated in a convection oven for 2 minutes at 70° C. to dissolve the photoinitiator.

The precursor composition was coated onto a microreplicated polypropylene film. The microreplicated polypropylene film of Examples 1 is described in WO 2007/070310 (Halverson et al.) and shown in FIG. 1. The film had at least two separate wells for retaining the precursor composition. The film had a short waffle shaped pattern in the bottom of the wells. The width of the square walls within the mold was about 250 micrometers, and the width of the land between each of the wells was about 20 micrometers. Each well was about 50 micrometers deep. The precursor composition was added to the film with a glass rod, such that the precursor composition was drawn into the wells of the mold by capillary action. The precursor composition was cured by passing the coated film under ultraviolet radiation using a belt processor available from Fusion UV Systems of Gaithersburg, Md. The belt processor was equipped with an H-bulb delivering a total UVA energy dose of 700 mJ/cm$^2$ (millijoules/square centimeter) in two passes to at least partially polymerize the polymerizable material of the precursor composition. The entire process was operated under ambient conditions. After exiting the UV source, the exposed polymeric material remained in the wells.

The swollen shaped polymeric materials remaining in the wells of the film were sprayed (i.e. spray bottle) with water. Upon hydration, the swollen shaped polymeric materials were squeezed out of the wells and collected to form swollen shaped polymeric materials.

FIG. 2 illustrates the swollen shaped polymeric materials replicating the dimensions and features of the wells in the film. The first swollen shaped polymeric materials were collected in the rinse water, and any remaining materials slowly settled to the bottom of the container. The clear, swollen shaped polymeric materials had a glossy appearance with no evidence of porosity. The swollen shaped polymeric materials had dimensions ranging from 222 micrometers to 238 micrometers, and a short waffle shaped pattern as found in the bottom of the wells. The swollen shaped polymeric materials were elastic, but could be crushed and were found to have a homogeneous composition throughout their make-up. An optical micrograph of the swollen shaped polymeric materials before drying is shown in FIG. 2. After collecting the swollen shaped polymeric materials, these materials were placed in a pan and dried in a convection oven for 2 hours at 85° C.

Example 2

Dried shaped polymeric materials of Example 1 were mixed with red food dye available from McCormick Foods of Sparks, Md. Dried shaped polymeric materials, 0.12 grams, were mixed with 0.375 grams of red food dye to form a mixture. The mixture was stirred continuously for about 5 minutes to distribute the red food dye. The shaped polymeric materials were then allowed to absorb the red food dye for about 1 hour. A red swollen shaped polymeric material, as a powder-like material, was observed. The red food dye swollen shaped polymeric materials had width dimensions of about 240 micrometers.

Example 3

Dried shaped polymeric materials formed in Example 1 were combined with an antimicrobial component. Dried shaped polymeric materials, 0.102 grams, were mixed with 0.463 grams of VANTOCIL P (antimicrobial active agent, 20 weight percent solids in water) commercially available from Arch Chemicals of Norwalk, Conn., to form a mixture. The mixture was stirred for about 1 minute, and then allowed to stand for about 1 hour. The mixture was filtered, and rinsed with deionized (DI) water to remove residual VANTOCIL P to form antimicrobial swollen shaped polymeric materials.

The antimicrobial swollen shaped polymeric materials were evaluated to determine antimicrobial activity using the Zone of Inhibition test method as described above. A zone of inhibition of 10.7 mm was measured with *Staphylococcus aureus* (gram positive(+)). A zone of inhibition of 18.7 mm was measured with *Pseudomonas aeruginosa* (gram negative (−)).

Examples 4-7

Dried shaped polymeric materials formed in Example 1 were loaded with active antimicrobial agents. Preparation 1 was prepared by mixing 0.5 grams of the dried shaped polymeric materials from Example 1 with 1 gram VANTOCIL 100 (antimicrobial active agent, 20 percent solids in water) commercially available from Arch Chemicals of Norwalk, Conn. Preparation 2 was prepared by mixing 0.5 grams of the dried shaped polymeric material from Example 1 with 1 gram VANTOCIL P-A (antimicrobial active agent, 20 percent solids in water) commercially available from Arch Chemical of Norwalk, Conn.

Preparations 1 and 2 were mixed separately, and allowed to equilibrate for 2 hours at room temperature. After two hours, water was added to Preparations 1 and 2 and they were shaken to wash away any unabsorbed biocides. Preparations 1 and 2 were then filtered, and washed a second time with water to form antimicrobial shaped polymeric materials. The antimicrobial shaped polymeric materials from Preparations 1 and 2 were dried slightly for approximately 5 minutes at room temperature (23° C.).

Preparations 1-2 and the other antimicrobial active agents described above were used in preparing the antimicrobial coatings of Examples 4-7. Antimicrobial coatings were prepared by mixing an acrylate resin commercially available from DSM NeoResins of Wilmington, Mass. under the trade designation, XK-90, with the antimicrobial compositions prepared above and water as listed in Table 1. Examples 4-7 were coated on a polyethylene terephthalate (PET) film commercially available from Mitsubishi Chemical of Japan. The antimicrobial coating was applied to the PET film using a Meyer rod #26. Examples 4-7 were dried for 10 minutes at 60° C. Examples 6 and 7 were prepared without the shaped polymeric materials. Examples 4 and 5 formed uniform coatings. Examples 6 and 7 formed nonuniform coatings with receded areas, and a slimy appearance.

Examples 4 and 5 of Table I were evaluated for antimicrobial activity using the Zone of Inhibition test method. Zone of Inhibition results were not recorded with Examples 6 and 7 due to poor coating uniformity. In Examples 4 and 5, a 7 millimeter (mm) circle was cut, and three circles were placed on each agar plate. The agar plates were inoculated with *Staphylococcus aureus* (gram positive (+)), or *Pseudomonas aeruginosa* (gram negative(−)). The compositions of Examples 4-7 and the Zone of Inhibition Assay results are shown in Table 1.

TABLE 1

(Antimicrobial Coatings)

| Example | Water (grams) | Resin (grams) | Antimicrobial Composition | Zone of Inhibition (mm) |
|---|---|---|---|---|
| 4 | 3 pt. (parts) | 5 pt XK-90 | Preparation 1 | 9.1 (gram+) 10.2 (gram−) |
| 5 | 3 pt. | 5 pt. XK-90 | Preparation 2 | 8.5 (gram+) 9 (gram−) |
| 6 | 3 pt. | 5 pt. XK-90 | VANTOCIL 100 | — |
| 7 | 3 pt. | 5 pt. XK-90 | VANTOCIL P-A | — |

Examples 4 and 5 showed antimicrobial properties in coatings using shaped polymeric materials.

Example 8

A precursor composition was prepared by combining and mixing 3.96 grams of 20-mole ethoxylated trimethylolpropane triacrylate ((TMPTA, SR-415)); 6 grams of deionized water; and 0.4 grams photoinitiator (IRGACURE 2959) in a container. The precursor composition was heated for 2 minutes at 70° C. to dissolve the photoinitiator.

The precursor composition was poured onto a metal tool having a raised 90 degree prismatic pattern at 60 micrometer spacing. The metal tool is described in Examples 1 and 2 of U.S. Pat. No. 5,175,030 (Lu et al.) and shown in FIG. 3. The precursor composition was uniformly spread over the metal tool surface covering the land, and overfilling the wells of the metal tool using a No. 40 Meyer rod. The metal tool coated with the precursor composition was passed under a 240 W/cm Fusion H bulb at a speed of 6 m/min (meters/minute) in a nitrogen atmosphere. The cured film was removed from the metal tool forming a shaped polymeric material having a continuous surface containing the inverse features of the wells formed on the surface of the film. The shaped polymeric materials were adjoined to the material on the land areas of the overfilled wells. What dried at 80° C. under reduced pressure overnight, the number of lines per unit area decreased due to the shrinkage that resulted from the loss of water. FIG. 4 illustrates the presence of shaped polymeric materials adjacent to one another which remain on the surface of the cured precursor composition after drying connected by land areas to form a film.

Example 9

Figure 3:
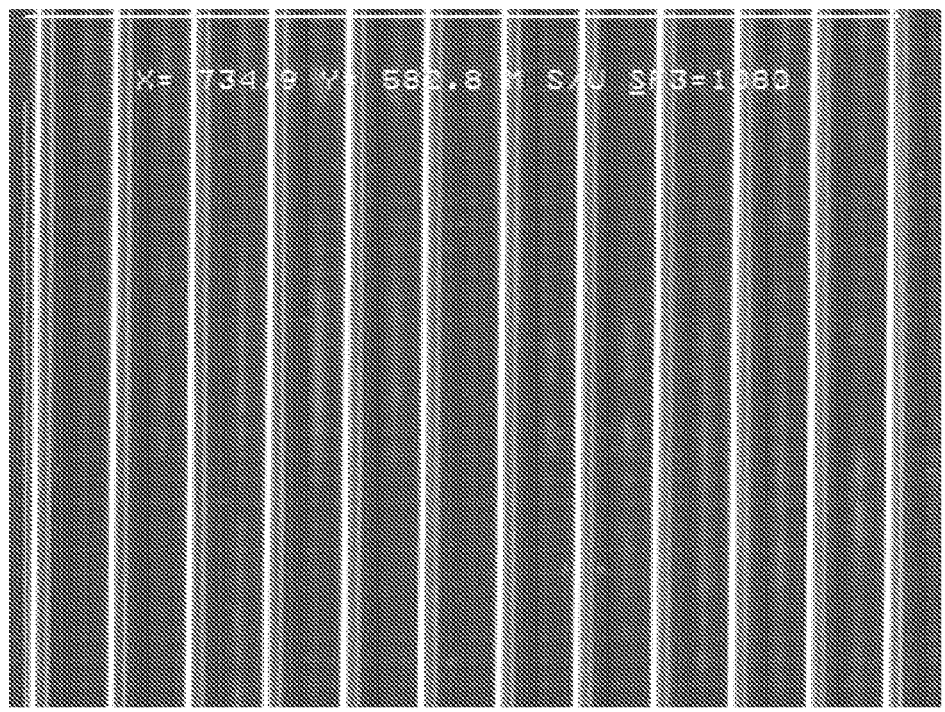
FIG. 3 is an optical micrograph of a metal tool of Example 8.
Figure 4:
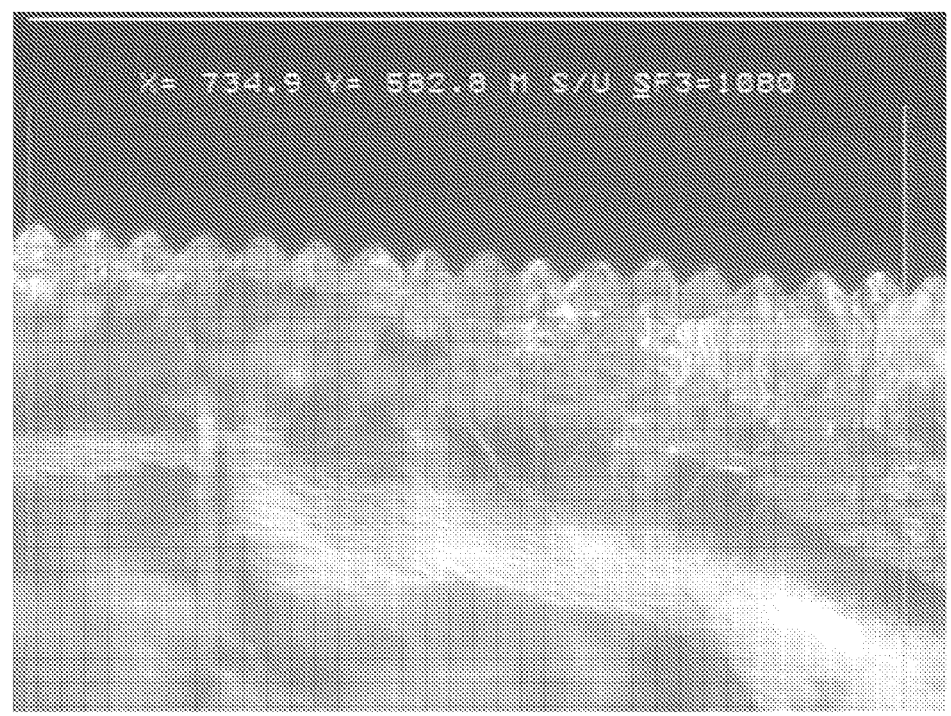
FIG. 4 is an optical micrograph of a cross-section of a film of Example 8.

The precursor composition of Example 8 was coated onto the metal tool of FIG. 3. The metal tool is described in Examples 1 and 2 of U.S. Pat. No. 5,175,030 (Lu et al.). The precursor composition coated onto the metal tool was covered with a 50 micrometer fluorinated copolymer film obtained from 3M Dyneon of St. Paul, Minn. under the trade designation THV 200 to form a multilayer structure. The multilayer structure was pulled through a fixed gap to spread the precursor composition across the surface of the metal tool. The multilayer structure was passed under a 240 W/cm Fusion H bulb at a speed of 6 m/minute. A cured film of the multilayer structure was formed. The multilayer structure was disassembled by removing the fluorinated copolymer film and recovering a shaped polymeric material adjoined by land areas.

Various modifications and alterations of this disclosure will be apparent to those skilled in the art without departing from the scope and spirit of this disclosure, and it should be understood that this disclosure is not limited to the illustrative elements set forth herein.

What is claimed is:

1. A method of making a shaped polymeric material comprising:
   providing a precursor composition comprising
      (a) at least 10 weight percent polar solvent based on the total weight of the precursor composition; and
      (b) no greater than 90 weight percent polymerizable material based on the total weight of the precursor composition, the polymerizable material being capable of free-radical polymerization and having an average number of ethylenically unsaturated groups per monomer molecule equal to at least 1.2, wherein the polymerizable material forms a single phase with the polar solvent and comprises a poly(alkylene oxide (meth)acrylate) having at least 2 (meth)acryloyl groups and having at least 5 alkylene oxide units, the poly(alkylene oxide(meth)acrylate) having a weight average molecular weight less than 2,000 g/mole;
   providing a mold having at least two separate wells;
   adding the precursor composition to the mold, the precursor composition being positioned in the at least two separate wells;
   exposing the precursor composition positioned in the at least two separate wells to radiation to at least partially polymerize the polymerizable material and to form a first swollen shaped polymeric material; and
   further comprising removing at least a portion of the polar solvent from the first swollen shaped polymeric material to form a dried shaped polymeric material, and contacting the dried shaped polymeric material with a sorbate for a time sufficient for the dried shaped polymeric material to sorb at least a portion of the sorbate to form a second swollen shaped polymeric material, wherein the sorbate comprises at least one active agent.

2. The method of claim 1, wherein the polymerizable material comprises a poly(alkylene oxide(meth)acrylate) having at least 3 (meth)acryloyl groups.

3. The method of claim 1, wherein the precursor composition further comprises a photoinitiator and the radiation comprises actinic radiation.

4. The method of claim 1, further comprising removing the first swollen shaped polymeric material from the mold.

5. The method of claim 4, wherein removing comprises applying a polar solvent to the first swollen shaped polymeric material.

6. The method of claim 1, further comprising drying the second swollen shaped polymeric material.

7. The method of claim 1, wherein adding the precursor composition to the mold comprises overfilling at least two separate wells, wherein the precursor composition resides on a first surface of the mold between the wells.

8. The method of claim 1, wherein the precursor composition further comprises an active agent.

9. The method of claim 8, wherein the active agent comprises a bioactive agent.

10. The method of claim 1, wherein the at least one active agent comprises a bioactive agent.

* * * * *